(12) United States Patent
Burke et al.

(10) Patent No.: US 9,334,285 B2
(45) Date of Patent: May 10, 2016

(54) ALDOSTERONE SYNTHASE INHIBITORS

(71) Applicant: Boehringer Ingelheim International GmbH, Ingelheim am Rhein (DE)

(72) Inventors: Jennifer Burke, Newtown, CT (US); Matthew A. Cerny, Oxford, CT (US); Derek Cogan, Ridgefield, CT (US); Kosea S. Frederick, Naugatuck, CT (US); John Lord, Poughkeepsie, NY (US); Daniel Richard Marshall, Norwalk, CT (US); Bryan P. McKibben, New Milford, CT (US); Simon Suprenant, New Milford, CT (US); Maolin Yu, Brookfield, CT (US); Yunlong Zhang, North Haven, CT (US); Lee Fader, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/806,706

(22) Filed: Jul. 23, 2015

(65) Prior Publication Data

US 2016/0024105 A1    Jan. 28, 2016

Related U.S. Application Data

(60) Provisional application No. 62/028,556, filed on Jul. 24, 2014.

(51) Int. Cl.
*C07D 491/052* (2006.01)
(52) U.S. Cl.
CPC .................. *C07D 491/052* (2013.01)
(58) Field of Classification Search
USPC ...................................... 548/303.1
See application file for complete search history.

(56) References Cited

U.S. PATENT DOCUMENTS

2014/0206886 A1* 7/2014 Scheidt ............. C07D 491/052
548/303.1

FOREIGN PATENT DOCUMENTS

| WO | 2007116099 A1 | 10/2007 |
| WO | 2007117982 A2 | 10/2007 |

OTHER PUBLICATIONS

International Search Report and Written Opinion, PCT, US 2015/041648, PCT/ISA/220, mailed Oct. 26, 2015.
Hartmann, et al, "Discovery of selective CYP11B2 (aldosterone synthase) inhibitors for the therapy of congestive heart failure and myocardial fibrosis", Euro. Journal of Medicinal Chamistry, vol. 38, No. 4, 2003.

* cited by examiner

*Primary Examiner* — Laura L. Stockton
(74) *Attorney, Agent, or Firm* — Michael P. Morris; Edward S. Lazer

(57) ABSTRACT

The present invention relates to compounds of formula I:

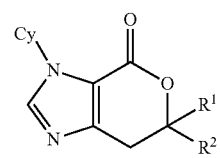

and pharmaceutically acceptable salts thereof, wherein Cy, $R^1$ and $R^2$ are as defined herein. The invention also relates to pharmaceutical compositions comprising these compounds, methods of using these compounds in the treatment of various diseases and disorders, processes for preparing these compounds and intermediates useful in these processes.

42 Claims, No Drawings

ALDOSTERONE SYNTHASE INHIBITORS

FIELD OF THE INVENTION

This invention relates to heteroaryl compounds that are useful as inhibitors of aldosterone synthase (CYP11B2) and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralcorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and profibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na^+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyzes the 3-step conversion of 11-deoxy-corticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by preclinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralcorticoid receptor (MR) activation, and much of the evidence favoring targeting this pathway comes from experiments with MR antagonists, non MR-mediated effects are reported and knockout mice for MR and aldosterone synthase exhibit different phenotypes. These observations further suggest that aldosterone synthase inhibitors may have a different profile and offer advantages compared to MR antagonists.

For example, several aldosterone actions are not inhibited by MR antagonists, including the including potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase (CYP11B2) and thus are useful for treating a variety of diseases and disorders that can be alleviated by lowering levels of aldosterone including renal disease, diabetic nephropathy, cardiovascular diseases and fibrotic disorders. In a further aspect, the invention provides compounds that are selective for inhibition of aldosterone synthase compared to cortisol synthase (CYP11B1), CYP17A1 and CYP19A1. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment of the invention, there are provided compounds of the formula I

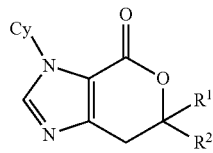

wherein:
Cy is a monocyclic or bicyclic ring system selected from $C_{3-10}$cycloalkyl, heterocyclyl, aryl and heteroaryl,
  wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl$)_2$, —$NH(C_{1-3}$-alkyl), —$NHCOC_{1-3}$-alkyl, —$C(O)C_{1-3}$-alkyl, —$C(O)OC_{1-3}$alkyl, hydroxy$C_{1-3}$alkyl, or heteroaryl;
$R^1$ and $R^2$ are independently selected from H, $C_{1-3}$alkyl, hydroxy$C_{1-3}$alkyl, —$CH_2NHC(O)OC_{1-4}$alkyl, —$CH_2OC(O)C_{1-4}$alkyl, —$C(O)OC_{1-4}$-alkyl, —$C(O)H$, —$COOH$, —$C(O)NHC_{1-4}$-alkyl and $C(O)N(C_{1-4}$-alkyl$)_2$, or $R^1$ and $R^2$ taken together form a $C_{3-6}$cycloalkyl or $C_{3-6}$-heterocyclyl;
or a salt thereof.

In another embodiment, there are provided compounds of the formula I as described according to the embodiment above and wherein Cy is a phenyl, cyclohexyl, indanyl, 2,3-dihydrobenzofuranyl or tetrahydroquinolinyl group, each optionally substituted with one, two, or three substituent groups independently selected from —Cl, —F, $C_{1-3}$alkyl, oxo and CN; and $R^1$ and $R^2$ are independently selected from H, $C_{1-3}$alkyl, hydroxy$C_{1-3}$alkyl, —$CH_2NHC(O)OC_{1-4}$alkyl, —$C(O)N(C_{1-4}$-alkyl$)_2$ and —$CH_2OC(O)C_{1-4}$alkyl.

In another embodiment, there are provided compounds of the formula I as described according to any of the embodiments above and wherein Cy is phenyl optionally substituted with one, two, or three substituent groups independently selected from —Cl, —F, $C_{1-3}$alkyl and CN.

In another embodiment, there are provided compounds of the formula I as described according to any of the embodiments above and wherein Cy is phenyl substituted with one, two, or three substituent groups independently selected from —Cl, —F, $C_{1-3}$alkyl and CN.

In another embodiment, there are provided compounds of the formula I as described according to any of the embodiments above and wherein Cy is phenyl substituted with CN and optionally substituted with one or two, additional groups independently selected from —Cl, —F and $C_{1-3}$alkyl.

In another embodiment, there are provided compounds of the formula I as described according to any of the embodiments above and wherein $R^1$ is —$CH_3$; and
$R^2$ is —$CH_3$ or —$CH_2OH$.

In another embodiment, there are provided compounds of the formula I as described according to any of the embodiments above and wherein $R^1$ is —$CH_3$; and
$R^2$ is —$CH_2OH$.

In another embodiment, there are provided compounds of the formula I as described according to any of the embodiments above and wherein $R^1$ is —$CH_3$; and
$R^2$ is —$CH_3$.

In another aspect of the invention, there is provided a compound of the general formula I according to any of the embodiments above, or a pharmaceutically acceptable salt thereof for use in a therapeutic method as described hereinbefore and hereinafter Table 1 shows representative compounds of the invention which can be made by the methods described in the general synthetic schemes, the examples, and known methods in the art.

TABLE 1

| Compound | Structure | Name |
|---|---|---|
| 1 | 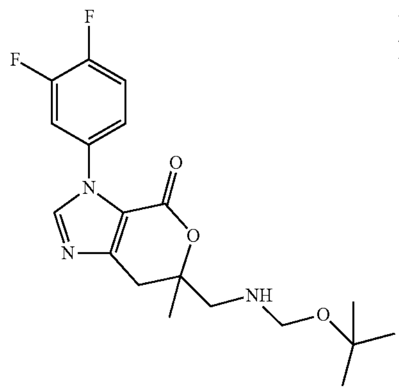 [SMILES: CC(C)(C)OCNCC1(C)Cc2ncn(-c3ccc(F)c(F)c3)c2C(=O)O1] | tert-butyl N{[3-(3,4-difluorophenyl)-6-methyl-4-oxo-3H,4H,6H,7H-pyrano[3,4-d]imidazol-6-yl]methyl}carbamate |
| 2 | 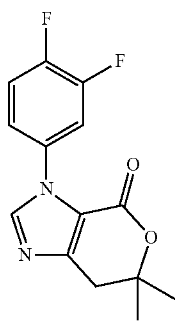 [SMILES: CC1(C)Cc2ncn(-c3ccc(F)c(F)c3)c2C(=O)O1] | 3-(3,4-difluorophenyl)-6,6-dimethyl-3H,4H,6H,7H-pyrano[3,4-d]imidazol-4-one |
| 3 | 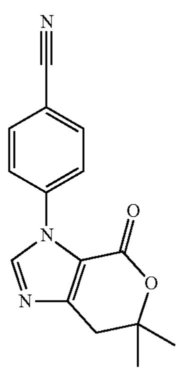 [SMILES: CC1(C)Cc2ncn(-c3ccc(C#N)cc3)c2C(=O)O1] | 4-{6,6-dimethyl-4-oxo-3H,4H,6H,7H-pyrano[3,4-d]imidazol-3-yl}benzonitrile |
| 4 | 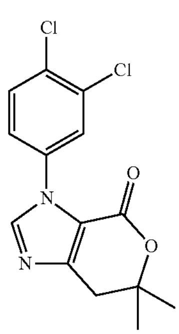 [SMILES: CC1(C)Cc2ncn(-c3ccc(Cl)c(Cl)c3)c2C(=O)O1] | 3-(3,4-dichlorophenyl)-6,6-dimethyl-3H,4H,6H,7H-pyrano[3,4-d]imidazol-4-one |

TABLE 1-continued

| Compound | Structure | Name |
|---|---|---|
| 5 | 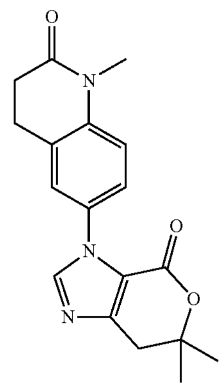 [SMILES: CN1C(=O)CCc2cc(-n3cnc4c3C(=O)OC(C)(C)C4)ccc21] | 6-{6,6-dimethyl-4-oxo-3H,4H,6H,7H-pyrano[3,4-d]imidazol-3-yl}-1-methyl-1,2,3,4-tetrahydroquinolin-2-one |
| 6 | 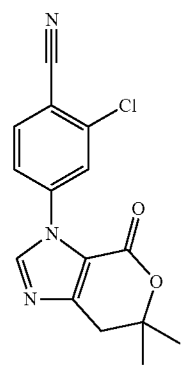 [SMILES: CC1(C)Cc2ncn(-c3ccc(C#N)c(Cl)c3)c2C(=O)O1] | 2-chloro-4-{6,6-dimethyl-4-oxo-3H,4H,6H,7H-pyrano[3,4-d]imidazol-3-yl}benzonitrile |
| 7 | 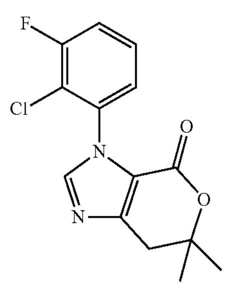 [SMILES: CC1(C)Cc2ncn(-c3cccc(F)c3Cl)c2C(=O)O1] | 3-(2-chloro-3-fluorophenyl)-6,6-dimethyl-3H,4H,6H,7H-pyrano[3,4-d]imidazol-4-one |
| 8 | 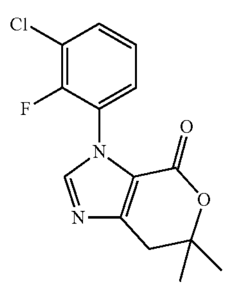 [SMILES: CC1(C)Cc2ncn(-c3cccc(Cl)c3F)c2C(=O)O1] | 3-(3-chloro-2-fluorophenyl)-6,6-dimethyl-3H,4H,6H,7H-pyrano[3,4-d]imidazol-4-one |

TABLE 1-continued

| Compound | Structure | Name |
| --- | --- | --- |
| 9 | 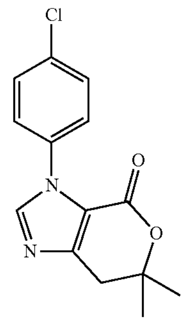 [SMILES: CC1(C)Cc2ncn(-c3ccc(Cl)cc3)c2C(=O)O1] | 3-(4-chlorophenyl)-6,6-dimethyl-3H,4H,6H,7H-pyrano[3,4-d]imidazol-4-one |
| 10 | 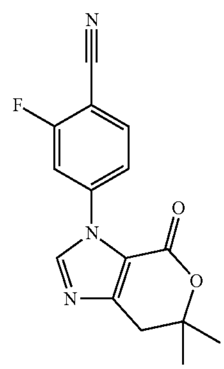 [SMILES: CC1(C)Cc2ncn(-c3ccc(C#N)c(F)c3)c2C(=O)O1] | 4-{6,6-dimethyl-4-oxo-3H,4H,6H,7H-pyrano[3,4-d]imidazol-3-yl}-2-fluorobenzonitrile |
| 11 | 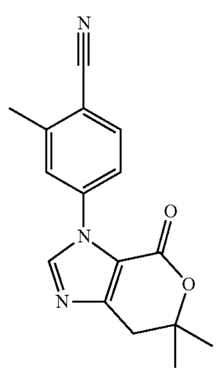 | 4-{6,6-dimethyl-4-oxo-3H,4H,6H,7H-pyrano[3,4-d]imidazol-3-yl}-2-methylbenzonitrile |
| 12 | 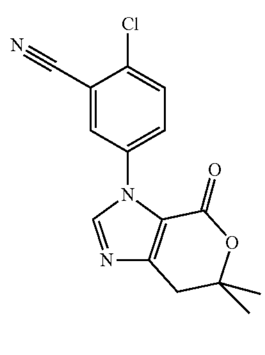 [SMILES: CC1(C)Cc2ncn(-c3ccc(Cl)c(C#N)c3)c2C(=O)O1] | 2-chloro-5-{6,6-dimethyl-4-oxo-3H,4H,6H,7H-pyrano[3,4-d]imidazol-3-yl}benzonitrile |

TABLE 1-continued

| Compound | Structure | Name |
| --- | --- | --- |
| 13 | 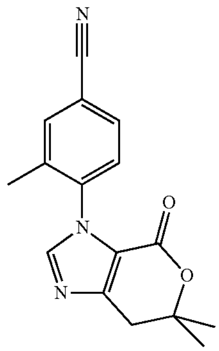 | 4-{6,6-dimethyl-4-oxo-3H,4H,6H,7H-pyrano[3,4-d]imidazol-3-yl}-3-methylbenzonitrile |
| 14 | 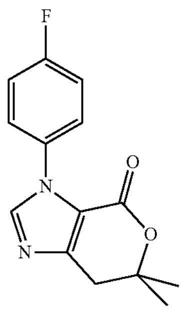 [SMILES: CC1(C)Cc2ncn(-c3ccc(F)cc3)c2C(=O)O1] | 3-(4-fluorophenyl)-6,6-dimethyl-3H,4H,6H,7H-pyrano[3,4-d]imidazol-4-one |
| 15 | 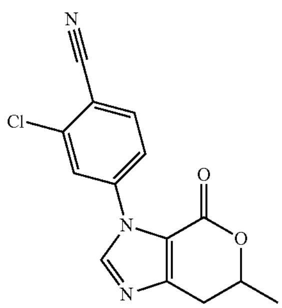 [SMILES: CC1Cc2ncn(-c3ccc(C#N)c(Cl)c3)c2C(=O)O1] | 2-chloro-4-[6-methyl-4-oxo-3H,4H,6H,7H-pyrano[3,4-d]imidazol-3-yl]benzonitrile |
| 16 | 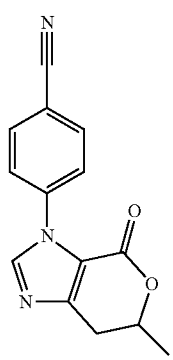 [SMILES: CC1Cc2ncn(-c3ccc(C#N)cc3)c2C(=O)O1] | 4[6-methyl-4-oxo-3H,4H,6H,7H-pyrano[3,4-d]imidazol-3-yl]benzonitrile |
| 17 | 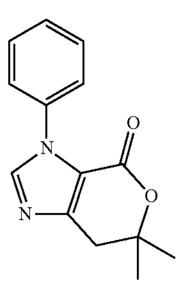 [SMILES: CC1(C)Cc2ncn(-c3ccccc3)c2C(=O)O1] | 6,6-dimethyl-3-phenyl-3H,4H,6H,7H-pyrano[3,4-d]imidazol-4-one |

TABLE 1-continued

| Compound | Structure | Name |
| --- | --- | --- |
| 18 | 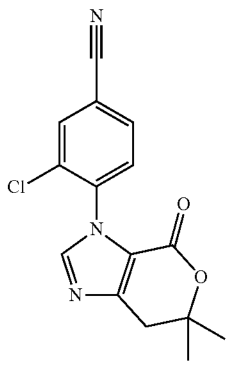 [SMILES: CC1(C)Cc2ncn(-c3ccc(C#N)cc3Cl)c2C(=O)O1] | 3-chloro-4-{6,6-dimethyl-4-oxo-3H,4H,6H,7H-pyrano[3,4-d]imidazol-3-yl}benzonitrile |
| 19 | 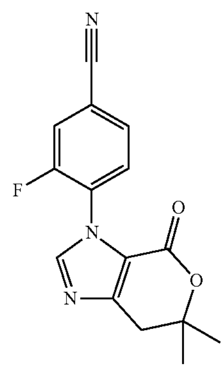 [SMILES: CC1(C)Cc2ncn(-c3ccc(C#N)cc3F)c2C(=O)O1] | 4-{6,6-dimethyl-4-oxo-3H,4H,6H,7H-pyrano[3,4-d]imidazol-3-yl}-3-fluorobenzonitrile |
| 20 | 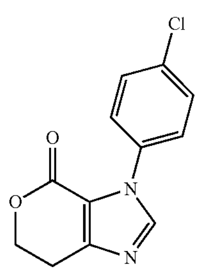 [SMILES: O=C1OCCc2ncn(-c3ccc(Cl)cc3)c21] | 3-(4-chlorophenyl)-3H,4H,6H,7H-pyrano[3,4-d]imidazol-4-one |
| 21 | 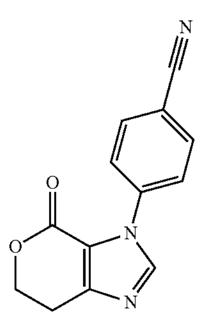 [SMILES: N#Cc1ccc(-n2cnc3c2C(=O)OCC3)cc1] | 4-{4-oxo-3H,4H,6H,7H-pyrano[3,4-d]imidazol-3-yl}benzonitrile |

TABLE 1-continued
| Compound | Structure | Name |
|---|---|---|
| 22 | 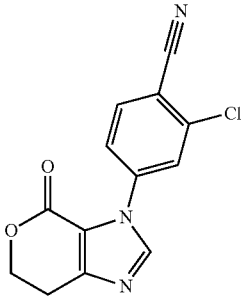 [SMILES: N#Cc1ccc(-n2cnc3c2C(=O)OCC3)cc1Cl] | 2-chloro-4-{4-oxo-3H,4H,6H,7H-pyrano[3,4-d]imidazol-3-yl}benzonitrile |
| 23 | 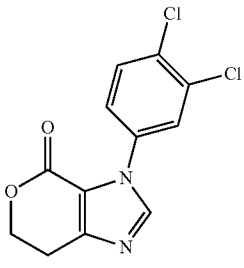 [SMILES: O=C1OCCc2ncn(-c3ccc(Cl)c(Cl)c3)c21] | 3-(3,4-dichlorophenyl)-3H,4H,6H,7H-pyrano[3,4-d]imidazol-4-one |
| 24 | 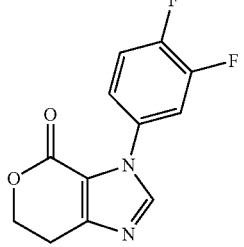 | 3-(3,4-difluorophenyl)-3H,4H,6H,7H-pyrano[3,4-d]imidazol-4-one |
| 25 | 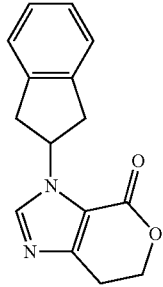 [SMILES: O=C1OCCc2ncn(C3Cc4ccccc4C3)c21] | 3-(2,3-dihydro-1H-inden-2-yl)-3H,4H,6H,7H-pyrano[3,4-d]imidazol-4-one |
| 26 | 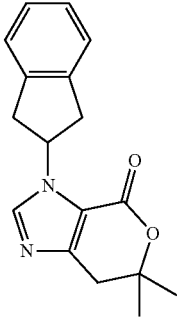 [SMILES: CC1(C)Cc2ncn(C3Cc4ccccc4C3)c2C(=O)O1] | 3-(2,3-dihydro-1H-inden-2-yl-6,6-dimethyl-3H,4H,6H,7H-pyrano[3,4-d]imidazol-4-one |

TABLE 1-continued

| Compound | Structure | Name |
|---|---|---|
| 27 | 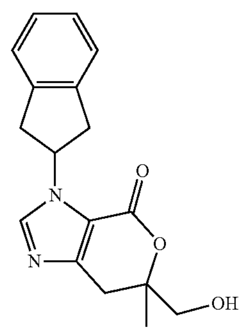 [SMILES: CC1(CO)Cc2ncn(C3Cc4ccccc4C3)c2C(=O)O1] | 3-(2,3-dihydro-1H-inden-2-yl)-6-(hydroxymethyl)-6-methyl-3H,4H,6H,7H-pyrano[3,4-d]imidazol-4-one |
| 28 | 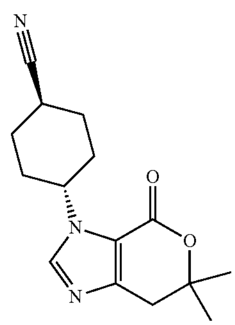 [SMILES: CC1(C)Cc2ncn([C@H]3CC[C@H](C#N)CC3)c2C(=O)O1] | trans-4-(6,6-Dimethyl-4-oxo-6,7-dihydro-4H-pyrano[3,4-d]imidazol-3-yl)-cyclohexanecarbonitrile |
| 29A | 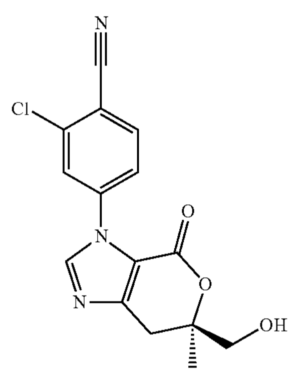 [SMILES: C[C@]1(CO)Cc2ncn(-c3ccc(C#N)c(Cl)c3)c2C(=O)O1] | 2-chloro-4-[(6R)-6-(hydroxymethyl)-6-methyl-4-oxo-3H,4H,6H,7H-pyrano[3,4-d]imidazol-3-yl]benzonitrile |
| 29B | 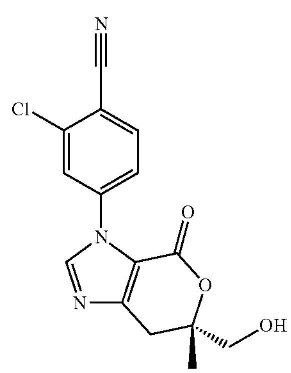 [SMILES: C[C@@]1(CO)Cc2ncn(-c3ccc(C#N)c(Cl)c3)c2C(=O)O1] | 2-chloro-4-[(6S)-6-(hydroxymethyl)-6-methyl-4-oxo-3H,4H,6H,7H-pyrano[3,4-d]imidazol-3-yl]benzonitrile |

TABLE 1-continued

| Compound | Structure | Name |
|---|---|---|
| 30 | 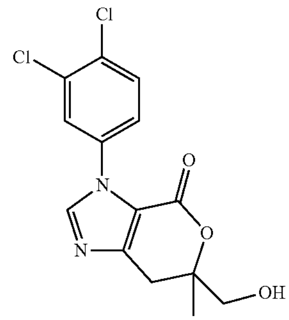 [SMILES: CC1(CO)Cc2ncn(-c3ccc(Cl)c(Cl)c3)c2C(=O)O1] | 3-(3,4-dichlorophenyl)-6-(hydroxymethyl)-6-methyl-3H,4H,6H,7H-pyrano[3,4-d]imidazol-4-one |
| 31 | 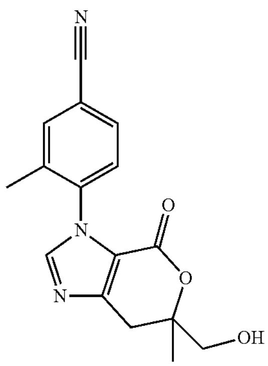 [SMILES: Cc1cc(C#N)ccc1-n1cnc2c1C(=O)OC(C)(CO)C2] | 4-[6-(hydroxymethyl)-6-methyl-4-oxo-3H,4H,6H,7H-pyrano[3,4-d]imidazol-3-yl]-3-methylbenzonitrile |
| 32 | 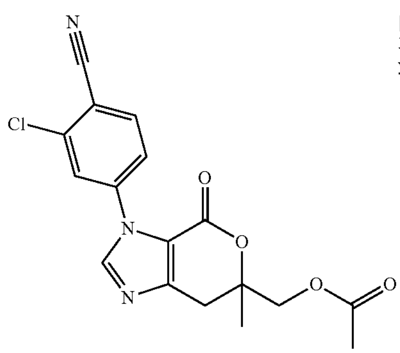 | [3-(3-chloro-4-cyanophenyl)-6-methyl-4-oxo-3H,4H,6H,7H-pyrano[3,4-d]imidazol-6-yl]methyl acetate |
| 33 | 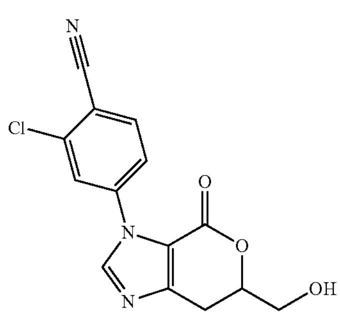 [SMILES: N#Cc1ccc(-n2cnc3c2C(=O)OC(CO)C3)cc1Cl] | 2-chloro-4-[6-(hydroxymethyl)-4-oxo-3H,4H,6H,7H-pyrano[3,4-d]imidazol-3-yl]benzonitrile |

TABLE 1-continued

| Compound | Structure | Name |
|---|---|---|
| 34 | 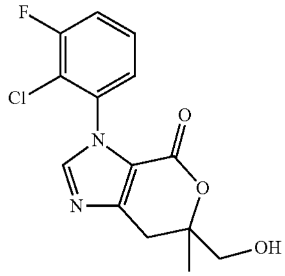 [SMILES: CC1(CO)Cc2ncn(-c3cccc(F)c3Cl)c2C(=O)O1] | 3-(2-chloro-3-fluorophenyl)-6-(hydroxymethyl)-6-methyl-3H,4H,6H,7H-pyrano[3,4-d]imidazol-4-one |
| 35 | 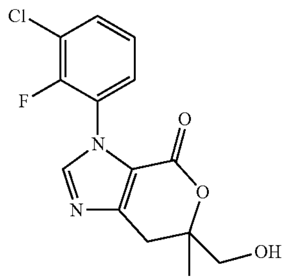 [SMILES: CC1(CO)Cc2ncn(-c3cccc(Cl)c3F)c2C(=O)O1] | 3-(3-chloro-2-fluorophenyl)-6-(hydroxymethyl)-6-methyl-3H,4H,6H,7H-pyrano[3,4-d]imidazol-4-one |
| 36 | 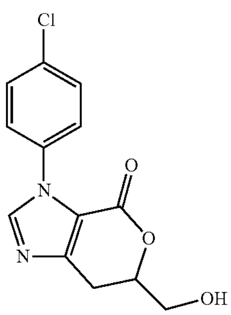 [SMILES: O=C1OC(CO)Cc2ncn(-c3ccc(Cl)cc3)c21] | 3-(4-chlorophenyl)-6-(hydroxymethyl)-3H,4H,6H,7H-pyrano[3,4-d]imidazol-4-one |
| 37 | 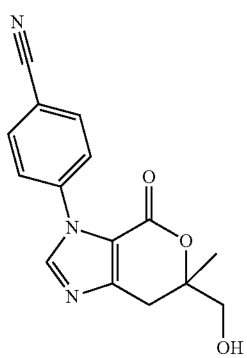 [SMILES: CC1(CO)Cc2ncn(-c3ccc(C#N)cc3)c2C(=O)O1] | 4-[6-(hydroxymethyl)-6-methyl-4-oxo-3H,4H,6H,7H-pyrano[3,4-d]imidazol-3-yl]benzonitrile |
| 38 | 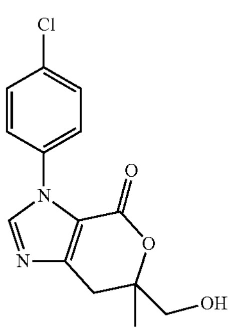 [SMILES: CC1(CO)Cc2ncn(-c3ccc(Cl)cc3)c2C(=O)O1] | 3-(4-chlorophenyl)-6-(hydroxymethyl)-6-methyl-3H,4H,6H,7H-pyrano[3,4-d]imidazol-4-one |

TABLE 1-continued

| Compound | Structure | Name |
|---|---|---|
| 39 | 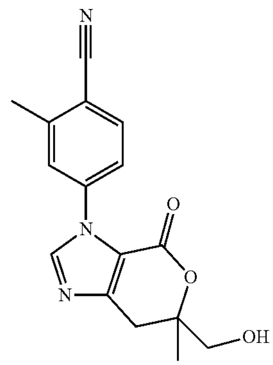 [SMILES: Cc1cc(-n2cnc3c2C(=O)OC(C)(CO)C3)ccc1C#N] | 4-[6-(hydroxymethyl)-6-methyl-4-oxo-3H,4H,6H,7H-pyrano[3,4-d]imidazol-3-yl]-2-methylbenzonitrile |
| 40 | 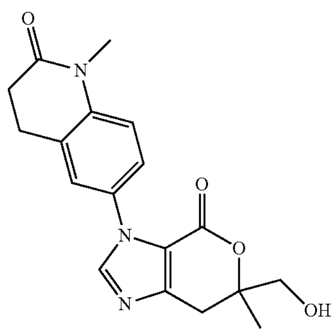 [SMILES: CN1C(=O)CCc2cc(-n3cnc4c3C(=O)OC(C)(CO)C4)ccc21] | 6-[(6R)-6-(hydroxymethyl)-6-methyl-4-oxo-3H,4H,6H,7H-pyrano[3,4-d]imidazol-3-yl]-1-methyl-1,2,3,4-tetrahydroquinolin-2-one |
| 41 | 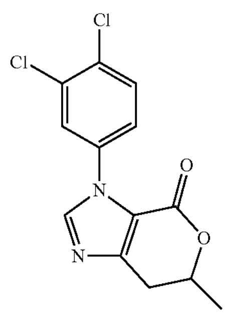 [SMILES: CC1Cc2ncn(-c3ccc(Cl)c(Cl)c3)c2C(=O)O1] | 3-(3,4-dichlorophenyl)-6-methyl-3H,4H,6H,7H-pyrano[3,4-d]imidazol-4-one |
| 42 | 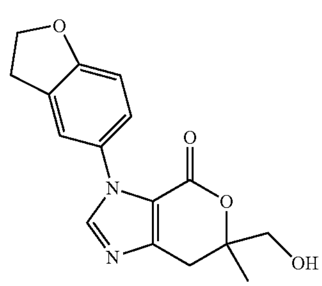 [SMILES: CC1(CO)Cc2ncn(-c3ccc4c(c3)CCO4)c2C(=O)O1] | 3-(2,3-Dihydro-benzofuran-5-yl)-6-hydroxymethyl-6-methyl-6,7-dihydro-3H-pyrano[3,4-d]imidazol-4-one |
| 43 | 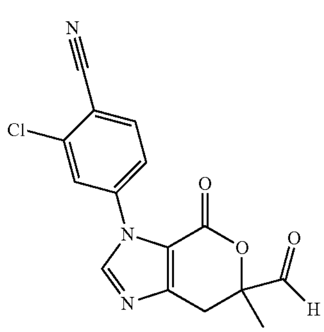 [SMILES: CC1(C=O)Cc2ncn(-c3ccc(C#N)c(Cl)c3)c2C(=O)O1] | 2-Chloro-4-(6-formyl-6-methyl-4-oxo-6,7-dihydro-4H-pyrano[3,4-d]imidazol-3-yl)-benzonitrile |

TABLE 1-continued

| Compound | Structure | Name |
|---|---|---|
| 44 | 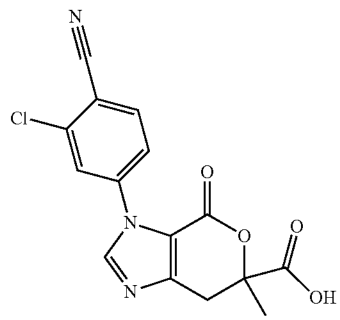 [SMILES: CC1(C(=O)O)Cc2ncn(-c3ccc(C#N)c(Cl)c3)c2C(=O)O1] | 3-(3-Chloro-4-cyano-phenyl)-6-methyl-4-oxo-3,4,6,7-tetrahydro-pyrano[3,4-d]imidazole-6-carboxylic acid |
| 45 | 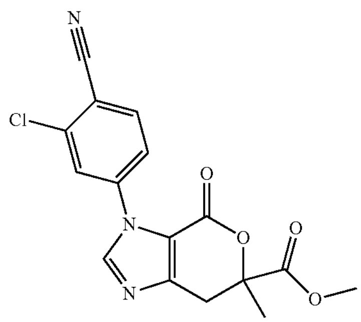 [SMILES: COC(=O)C1(C)Cc2ncn(-c3ccc(C#N)c(Cl)c3)c2C(=O)O1] | 3-(3-Chloro-4-cyano-phenyl)-6-methyl-4-oxo-3,4,6,7-tetrahydro-pyrano[3,4-d]imidazole-6-carboxylic acid methyl ester |
| 46 | 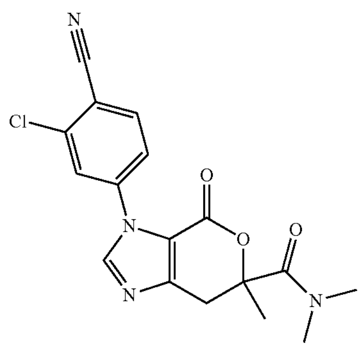 [SMILES: CN(C)C(=O)C1(C)Cc2ncn(-c3ccc(C#N)c(Cl)c3)c2C(=O)O1] | Chloro-4-cyano-phenyl)-6-methyl-4-oxo-3,4,6,7-tetrahydro-pyrano[3,4-d]imidazole-6-carboxylic acid dimethylamide |

In one embodiment, the invention relates to compounds 1-46 depicted in Table 1 above and the pharmaceutically acceptable salts thereof.

In another embodiment, the invention relates to compounds 1-11, 13, 15, 18, 19, 22, 23, 26, 28, 29A, 29B, 30-33, 35, 39, 41, 42, 45 and 46 depicted in Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g.,$^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_3$))—, —(CHCH(CH$_3$)$_2$)— and —C(CH$_3$)(CH$_2$CH$_3$)—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3] heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$alkyl, likewise, —S—$R_a$ may be represented as phenyl-S(O)$_m$— when $R_a$ is phenyl and where m is 0, 1 or 2.

GENERAL SYNTHETIC METHODS

The compounds of the invention may be prepared by the methods and examples presented below and methods known to those of ordinary skill in the art. The methods that are described here are intended as an illustration and for the enablement of the instant invention without restricting the scope of its subject matter, the claimed compounds, and the examples. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Compounds of formula (I) may be prepared as illustrated in Scheme 1

Scheme 1

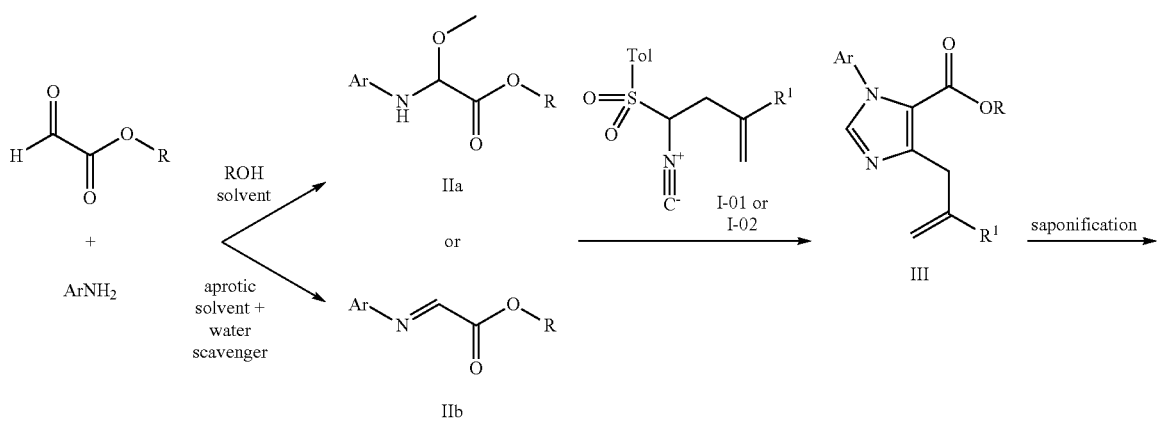

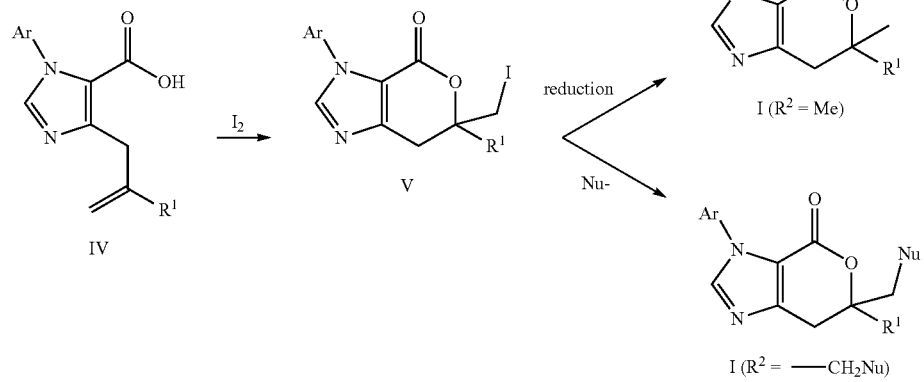

As illustrated in Scheme 1, a 2-oxoacetic acid ester may be reacted with optionally substituted aniline in a suitable protic solvent such as methanol to provide intermediate IIa. Alternatively, reaction in an aprotic solvent such as toluene, in the presence of a suitable water scavenger such as anhydrous $Na_2SO_4$ provides intermediate IIb. Reaction of IIa or IIb with intermediate I-01 or I-02 in a suitable solvent such as EtOH in the presence of a suitable base such as $K_2CO_3$ provides intermediate of formula III. Hydrolysis of ester III provides carboxylic acid IV. Reaction of IV with $I_2$ in a suitable solvent such as THF in the presence of a suitable base such as $NaHCO_3$ provides intermediate of formula V. Reduction of lactone V with a suitable reducing agent such as $Bu_3SnH$/AIBN provides the desired compound of formula I having Cy=optionally substituted Ar, X=a bond and $R^2$=methyl. Alternatively, displacement of the I in intermediate V with a nucleophile NuH provides the compound of formula I having Cy=optionally substituted Ar and $R^2$=—$CH_2Nu$.

Compounds of formula I having $R^2$=—$CH_2OH$ may be prepared by reaction of intermediate IV with a suitable peracid such as m-chloroperoxybenzoic acid (mCPBA) as shown in Scheme 2.

Scheme 2

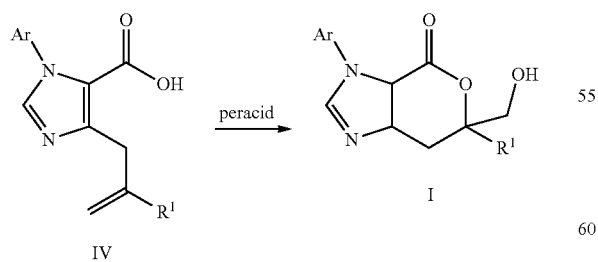

A method to prepare intermediate XXII, which may be used to prepare compounds of formula I, is illustrated in Scheme 3

Scheme 3

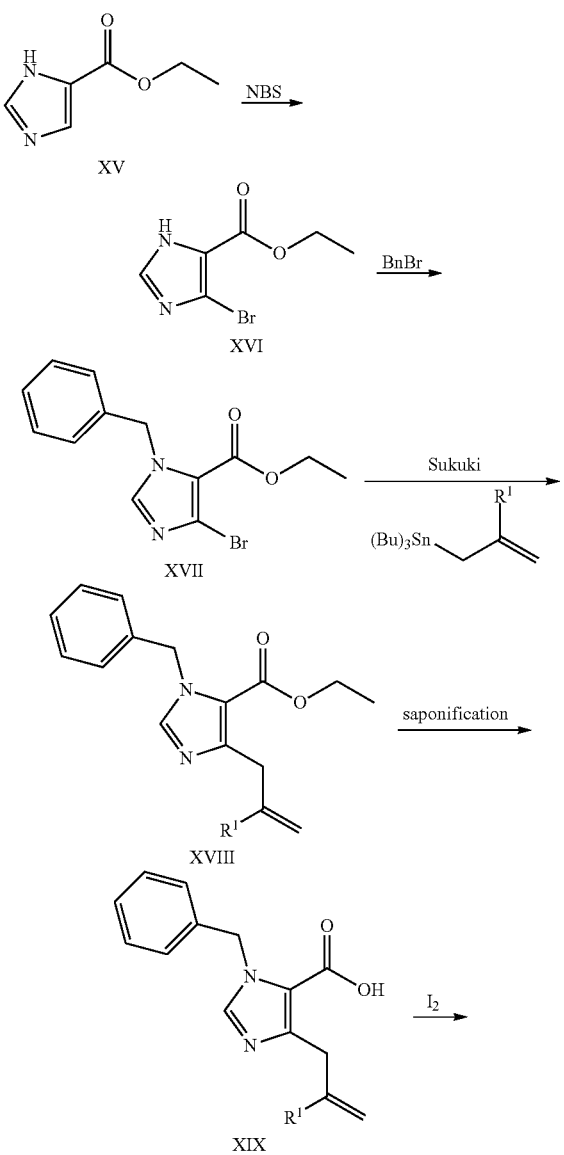

-continued

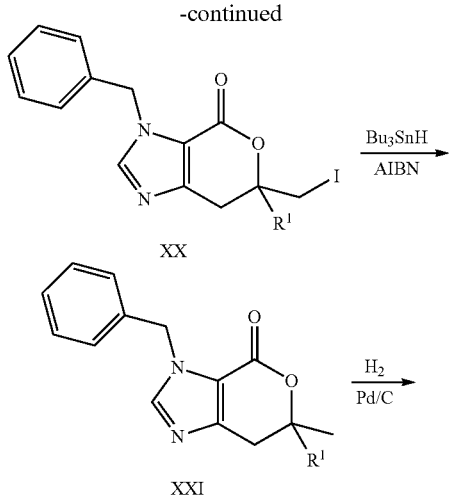

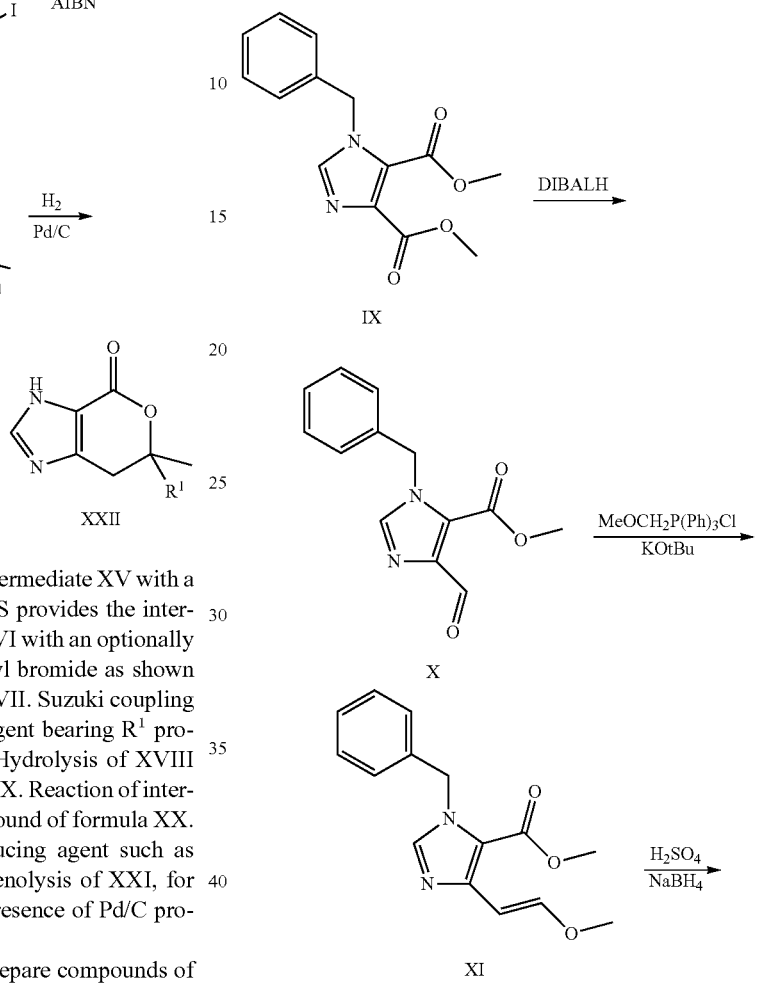

Additionally, compounds of formula I having hydrogen at both $R^1$ and $R^2$ may be prepared from intermediate XIV, which may be synthesized as illustrated in Scheme 5.

Scheme 5

As shown in Scheme 3, reaction of intermediate XV with a suitable brominating agent such as NBS provides the intermediate of formula XVI. Reaction of XVI with an optionally substituted benzyl halide such as benzyl bromide as shown provides the intermediate of formula XVII. Suzuki coupling of XVII with a suitable tributyl tin reagent bearing $R^1$ provides intermediate of formula XVIII. Hydrolysis of XVIII provides a carboxylic acid of formula XIX. Reaction of intermediate XIX with $I_2$ provides the compound of formula XX. Reduction of XX with a suitable reducing agent such as $Bu_3SnH/AIBN$ provides XXI. Hydrogenolysis of XXI, for example by treatment with $H_2$ in the presence of Pd/C provides XXII.

Intermediate XXII may be used to prepare compounds of formula I as shown in Scheme 4 and the synthetic examples.

Scheme 4

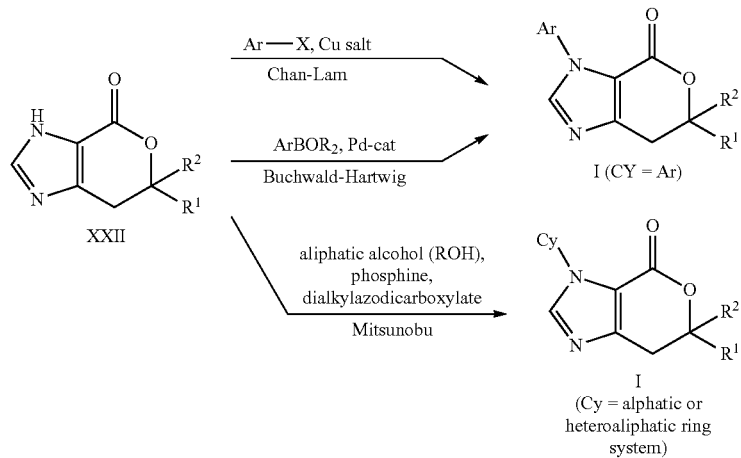

-continued

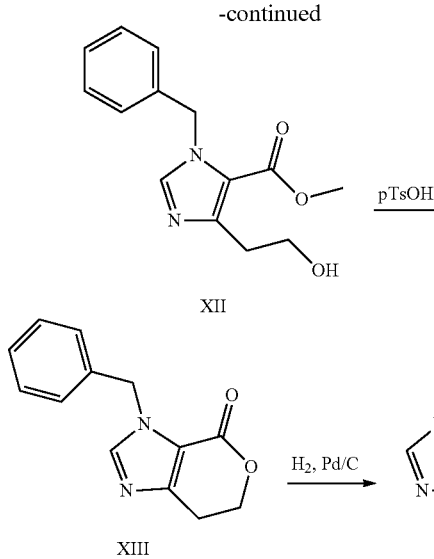

As shown in Scheme 5, reduction of diester intermediate of formula IX with a suitable reagent such as DIBALH provides aldehyde X. Wittig reaction of X provides olefin XI, which is reduced to provide intermediate XII. Lactonization of acid XII in the presence of a suitable acid such as p-TsOH provides intermediate of formula XIII. Hydrogenolysis of XIII provides intermediate XIV, which may be used to make additional compounds of formula I as shown for intermediate XXII in Scheme 4.

SYNTHETIC EXAMPLES

Final compounds are designated by compound numbers corresponding to the compound numbers in Table 1. Compounds that are resolved by chiral HPLC are done so by the conditions described in the Examples below. The first to elute is designated enantiomer A, and the second to elute is enantiomer B.

Synthesis of 1-(1-isocyano-3-methyl-but-3-enyl) sulfonyl-4-methyl-benzene (I-01)

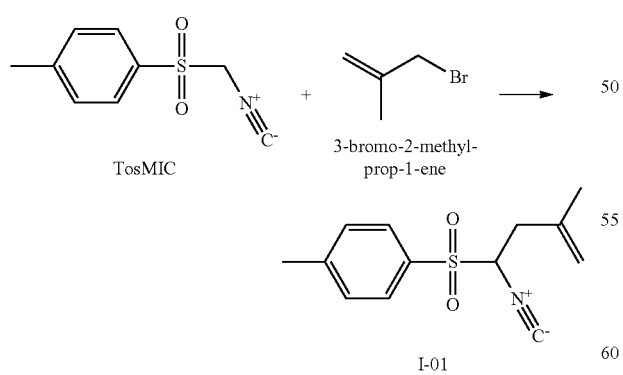

To a stirred and cooled (0° C.) solution of 4.0 g (20 mmol) of toluenemethyl isocyanate (TosMIC) in 50 mL of CH$_2$Cl$_2$ are added 1.5 g (4 mmol) of tetrabutylammonium iodide, 2.6 mL (25 mmol) of 3-bromo-2-methyl-prop-1-ene and 40 mL of 30% aqueous NaOH. The mixture is vigorously stirred for 3 h, and then diluted with H$_2$O. The layers are separated and extracted with CH$_2$Cl$_2$. The combined extracts are washed with H$_2$O, brine, dried (MgSO$_4$), filtered and concentrated to give a residue that is dissolved in ether/EtOAc and extracted twice each with 100 mL of H$_2$O. The organic phase is dried with MgSO$_4$, filtered and concentrated to provide 5.0 g of compound I-01 that is used directly without purification.

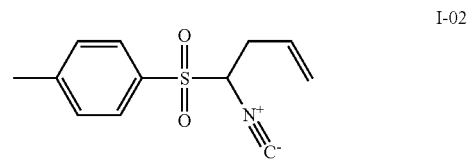 [SMILES: [C-]#[N+]C(CC=C)S(=O)(=O)c1ccc(C)cc1]

Compound I-02 is prepared in the same manner as compound I-01 using allyl bromide in the place of 3-bromo-2-methyl-prop-1-ene.

Synthesis of ethyl 2-(3,4-difluoroanilino)-2-methoxy-acetate (I-03a)

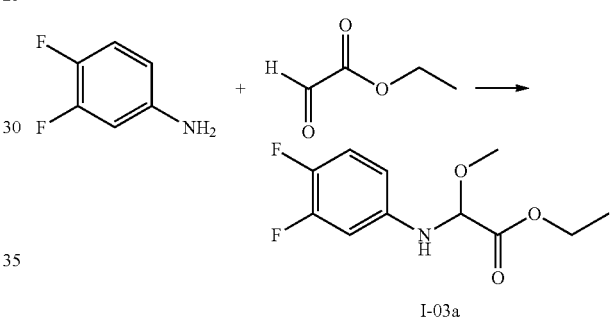

To a stirred solution of 2.0 g (15 mmol) of 3,4-difluoroaniline in methanol is added 4.0 g (39 mmol) of ethyl 2-oxoacetate. After stirring for 14 h, the mixture is concentrated to provide 3.7 g of I-03a that is used directly without purification.

The following 2-arylamino-2-methoxyacetates I-03b through l are prepared in the same manner as I-03a using the analogous arylamine.

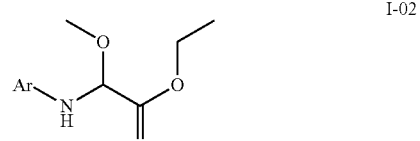

I-03b: Ar=4-cyanophenyl
I-03c: Ar=3,4-dichlorophenyl
I-03d: Ar=1-methyl-3,4-dihydroquinolin-2-one-6-yl
I-03e: Ar=3-chloro-4-cyanophenyl
I-03f: Ar=2-chloro-3-fluorophenyl
I-03g: Ar=2-fluoro-3-chlorophenyl
I-03h: Ar=4-chlorophenyl
I-03i: Ar=3-fluoro-4-cyanophenyl
I-03j: Ar=3-methyl-4-cyanophenyl
I-03k: Ar=2-chloro-4-cyanophenyl
I-03l: Ar=2-fluoro-4-cyanophenyl Synthesis of 4-chloro-3-cyano-phenylimino-acetic acid ethyl ester (I-04m)

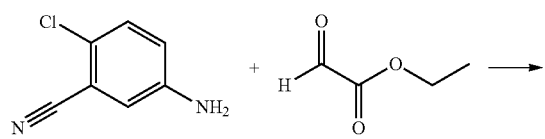

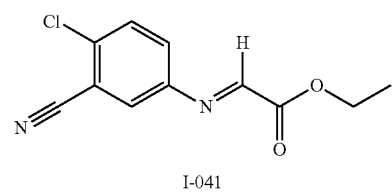

A mixture of 1.3 mL (6.6 mmol) of ethyl glyoxal 50% in toluene, 1.0 g (6.6 mmol) of 5-amino-2-chlorobenzonitrile, toluene (85 ml) and 11 g (33 mmol) of $NaSO_4$ is heated at reflux for 2 h. The mixture is cooled, filtered and concentrated to provide 1.6 g of I-04m that is used directly.

The following imines I-04n and o are prepared in the analogous manner to I-04m using the appropriate arylamine.

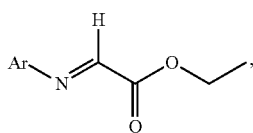

I-04n: Ar=2-methyl-4-cyanophenyl
I-04o: Ar=4-fluorophenyl

Synthesis of 3-(3,4-difluoro-phenyl)-5-(2-methyl-allyl)-3H-imidazole-4-carboxylic acid ethyl ester (I-05a)

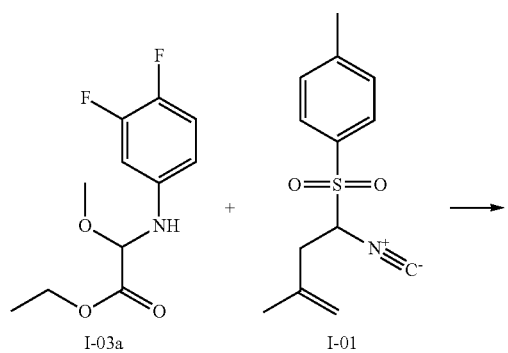

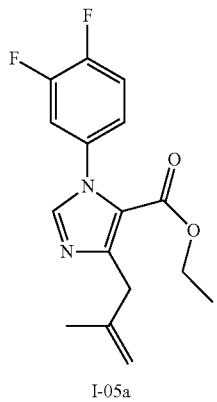

To a stirred solution of 10 g (41 mmol) of I-01 in ethanol is added 20 g (80 mmol) of I-03a and 23 g (160 mmol) of $K_2CO_3$. After heating at reflux for 5 h, the mixture is cooled to rt and water is added. The mixture is extracted with EtOAc and the extract is concentrated. The concentrate is chromatographed (30% EtOAc/petroleum ether) to provide 2.1 g of I-05a.

The following imidazoles I-05b through I-05l are prepared in the same manner as I-05a using I-01 and the appropriate intermediates I-03b through I-03l.

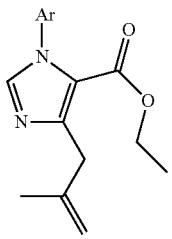

I-05b: Ar=4-cyanophenyl
I-05c: Ar=3,4-dichlorophenyl
I-05d: Ar=1-methyl-3,4-dihydroquinolin-2-one-6-yl
I-05e: Ar=3-chloro-4-cyanophenyl
I-05f: Ar=2-chloro-3-fluorophenyl
I-05g: Ar=2-fluoro-3-chlorophenyl
I-05h: Ar=4-chlorophenyl
I-05i: Ar=3-fluoro-4-cyanophenyl
I-05j: Ar=3-methyl-4-cyanophenyl
I-05k: Ar=2-chloro-4-cyanophenyl
I-05l: Ar=2-fluoro-4-cyanophenyl The following imidazoles I-05m, n and o are prepared in the same manner as I-05a using I-01 and the appropriate imines I-04m, n and o in place of I-03a.

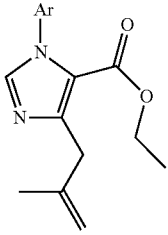

I-05m: Ar=3-cyano-4-chlorophenyl
I-05n: Ar=2-methyl-4-cyanophenyl
I-05o: Ar=4-fluorophenyl The following imidazoles I-06b, e, and h are prepared in the same manner as I-05a using I-02 and the appropriate intermediates I-03b, e, and h.

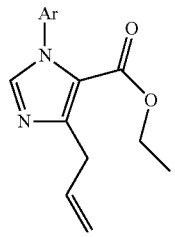

I-06b,e,h

I-06b: Ar=4-cyanophenyl
I-06e: Ar=3-chloro-4-cyanophenyl
I-06h: Ar=4-chlorophenyl Synthesis of 3-(3,4-difluorophenyl)-5-(2-methylallyl)imidazole-4-carboxylic acid (I-07a)

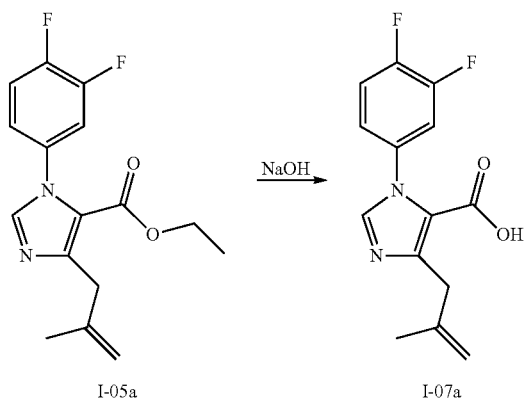

I-05a     I-07a

To a stirred solution of 0.67 g (2.2 mmol) of I-05a in EtOH and THF and is added 0.26 g (6.6) of NaOH in H₂O. After stirring for 12 h, acetic acid is added until the pH of the mixture is acidic, and the mixture is concentrated to provide 0.61 g (2.2 mmol) of I-07a.

The following acids I-07b, c, and d are prepared in the same manner as I-07a from the appropriate olefins I-05b, c, and d.

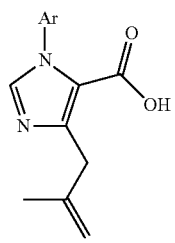

I-07b,c,d

I-07b: Ar=4-cyanophenyl
I-07c: Ar=3,4-dichlorophenyl
I-07d: Ar=1-methyl-3,4-dihydroquinolin-2-one-6-yl Synthesis of 2-chloro-4-[6-(iodomethyl)-6-methyl-4-oxo-7H-pyrano[3,4-d]imidazol-3-yl]benzonitrile (I-07e)

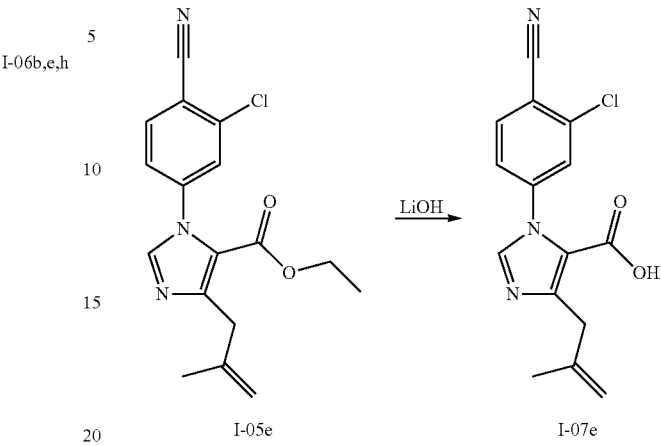

I-05e     I-07e

To a stirring solution of 5.0 g (15 mmol) of I-05e in 125 mL of a 3:1 mixture of THF/H₂O is 0.83 g (19 mmol) of LiOH hydrate. After 16 h, 80 mL of 3:1THF/H₂O is added. After 8 h, 10 mL of EtOH is added. After 40 h the mixture is concentrated and acidified by the addition of AcOH. The resulting precipitate is collected via filtration and dried to give 4.0 g (13 mmol) of I-07e.

The following acids I-07f, g, h, i, j, l, m, and n are prepared in the same manner as I-07e from the appropriate olefins I-07f, g, h, i, j, l, m, and n.

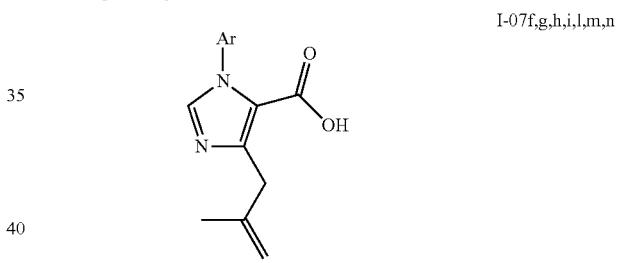

I-07f,g,h,i,l,m,n

I-07f: Ar=2-chloro-3-fluorophenyl
I-07g: Ar=2-fluoro-3-chlorophenyl
I-07h: Ar=4-chlorophenyl
I-07i: Ar=3-fluoro-4-cyanophenyl
I-07j: Ar=3-methyl-4-cyanophenyl
I-07m: Ar=3-cyano-4-chlorophenyl
I-07n: Ar=2-methyl-4-cyanophenyl
I-07o: Ar=4-fluorophenyl The following acids I-8b, e, and h are prepared in the same manner as I-07e from the appropriate olefins I-06b, e, and h.

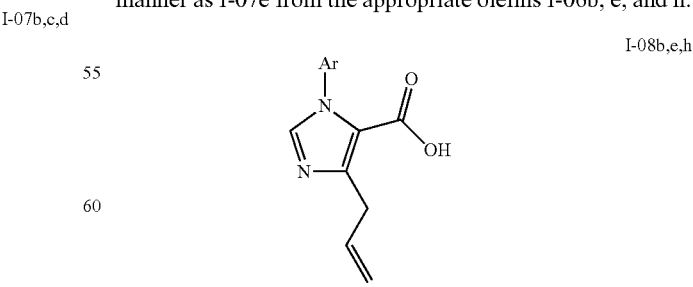

I-08b,e,h

I-08b: Ar=4-cyanophenyl
I-08e: Ar=3-chloro-4-cyanophenyl
I-08h: Ar=4-chlorophenyl Synthesis of 3-(3,4-difluorophenyl)-6-(iodomethyl)-6-methyl-7H-pyrano[3,4-d]imidazol-4-one (I-09a)

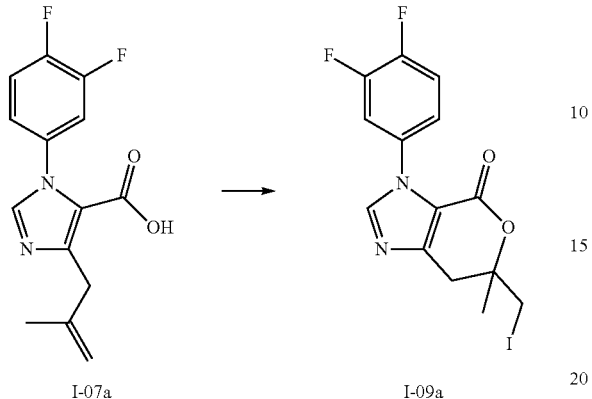

I-07a → I-09a

I-07a (0.61 g, 2.2 mmol) is dissolved in THF and cooled to 0° C. NaHCO$_3$ (0.74 g, 8.8 mmol) and I$_2$ (1.7 g, 6.6 mmol) are added and the mixture is stirred at 0° C. for 2 h. Aqueous Na$_2$S$_2$O$_3$ is added and the mixture is extracted twice with EtOAc. The combined extracts are washed with H$_2$O, brine and concentrated. Flash chromatography (0-100% EtOAc/heptanes) provides 0.89 g of I-09a.

The following iodides I-09b through j and m, n and o are prepared in the same manner as I-09a from the appropriate olefins I-09b through j and m, n and o.

I-09b,c,d,e,f,g,h,i,j,m,n,o

I-09b: Ar=4-cyanophenyl
I-09c: Ar=3,4-dichlorophenyl
I-09d: Ar=1-methyl-3,4-dihydroquinolin-2-one-6-yl
I-09e: Ar=3-chloro-4-cyanophenyl
I-09f: Ar=2-chloro-3-fluorophenyl
I-09g: Ar=2-fluoro-3-chlorophenyl
I-09h: Ar=4-chlorophenyl
I-09i: Ar=3-fluoro-4-cyanophenyl
I-09j: Ar=3-methyl-4-cyanophenyl
I-09m: Ar=3-cyano-4-chlorophenyl
I-09n: Ar=2-methyl-4-cyanophenyl
I-09o: Ar=4-fluorophenyl The following iodides I-10b and e are prepared in the same manner as I-09a from the appropriate olefins I-8b and e.

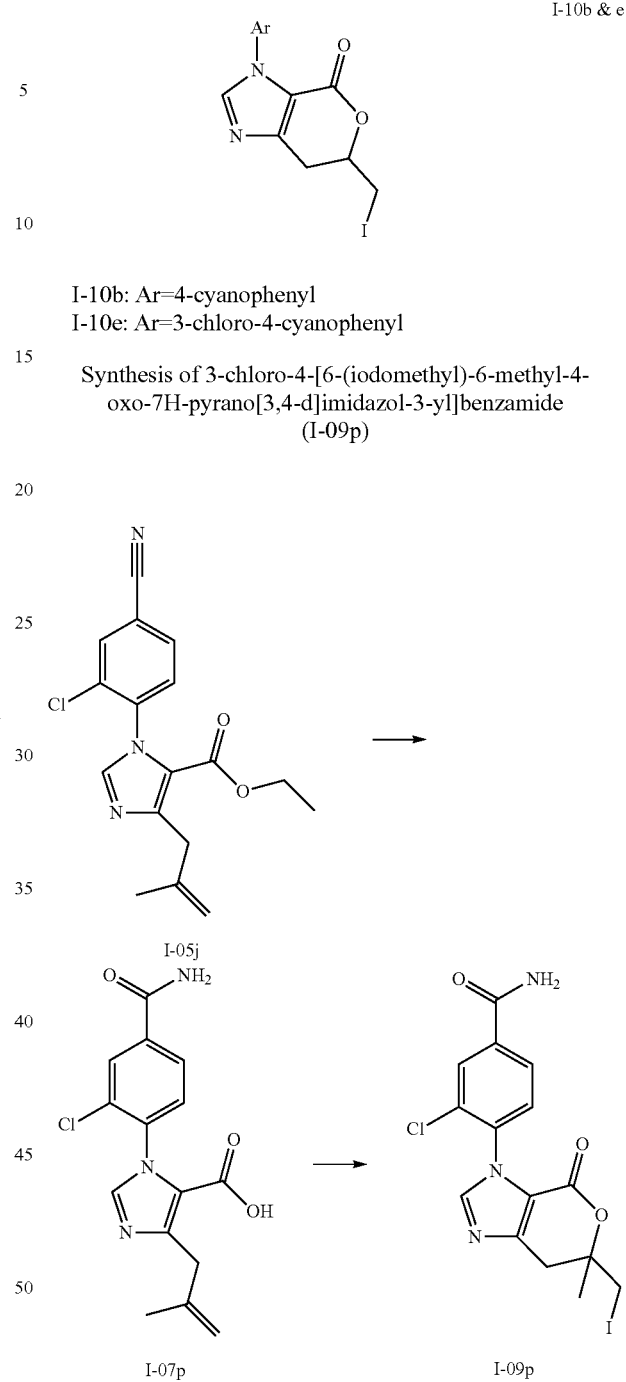

I-10b & e

I-10b: Ar=4-cyanophenyl
I-10e: Ar=3-chloro-4-cyanophenyl

Synthesis of 3-chloro-4-[6-(iodomethyl)-6-methyl-4-oxo-7H-pyrano[3,4-d]imidazol-3-yl]benzamide (I-09p)

I-05j

I-07p → I-09p

To a stirring mixture of 0.61 g (1.9 mmol) of I-05k in a 3/2 mixture of THF/H$_2$O is added 0.10 g (2.4 mmol) of LiOH hydrate. After 16 h, 100 mg of LiOH hydrate is added and the mixture stirred for 4 h and 4 mL of EtOH and 4 mL of H$_2$O are added. After stirring for 72 h, the mixture is concentrated, the resulting residue suspended in 20 mL of H$_2$O and AcOH added until the pH is acidic. The mixture is extracted with 2×100 mL of EtOAc and the extract washed with 40 mL of brine, dried over MgSO$_4$, filtered and concentrated to give 486 mg I-07p in 80% purity that is stirred in CH$_3$CN and cooled to 0° C. NaHCO$_3$ (0.51 g, 6.1 mmol) and 1.2 g (4.6 mmol) of I$_2$ are added and the mixture is stirred at 0° C. for 2 h. Aqueous Na$_2$S$_2$O$_3$ is added and the mixture is extracted twice with EtOAc. The combined extracts are washed with H$_2$O, brine and concentrated. Flash chromatography (0-100% EtOAc/heptanes) provides 0.57 g of I-09p.

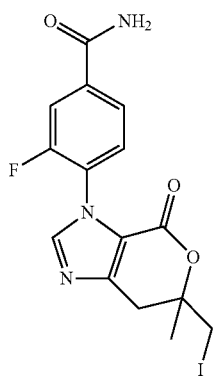

I-09q

Compound I-09q is prepared from I-051 in the same manner as compound I-09p.

Synthesis of 6,7-dihydro-3H-pyrano[3,4-d]imidazol-4-one (I-16)

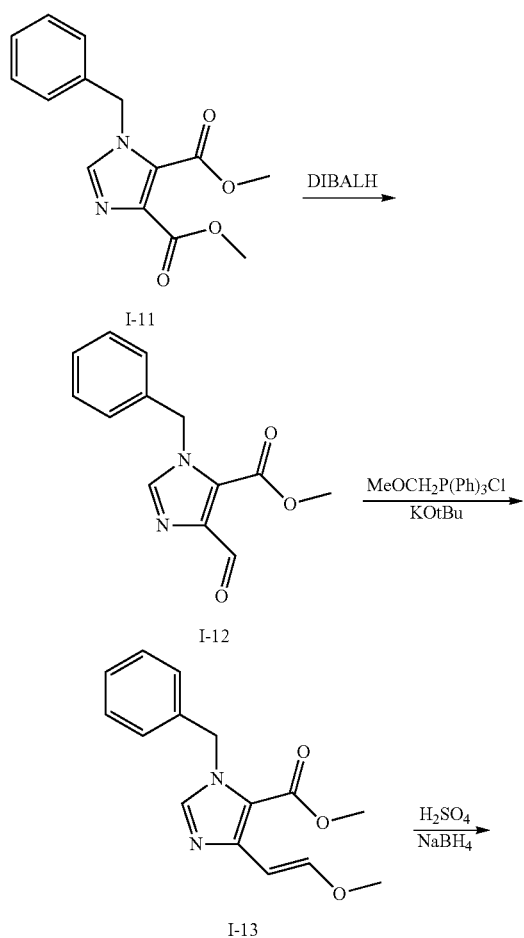

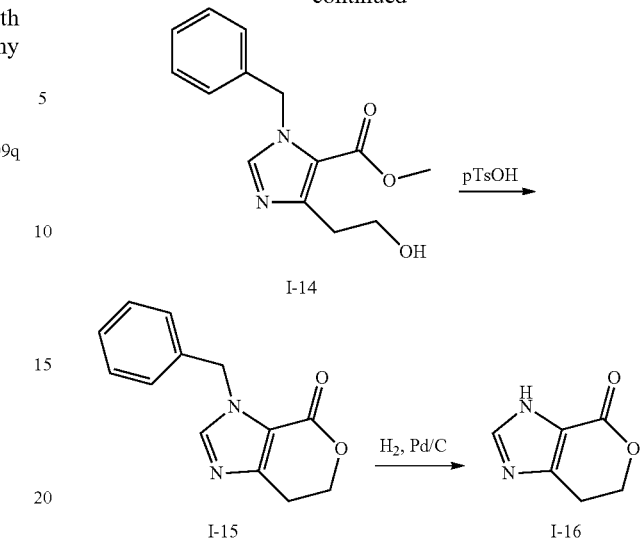

To a stirring mixture of I-11 (Haolun, J. et al., *Bioorg. Medicinal Chem. Lett,* 2006, 16, 3985) 10 g (37 mmol) in 100 mL of THF at −78° C. is added 52 mL (52 mmol) of 1M DIBAL-H in THF and the reaction mixture is stirred −78° C. for 2 h. Then water is slowly added and the reaction mixture is extracted with ethyl acetate. The organic layer is dried over Na$_2$SO$_4$, filtered, and concentrated to provide I-12 that is used without further purification.

To a suspension of 3.9 g (12 mmol) of methoxymethyltriphenylphosphonium chloride in THF (25 ml) at 0° C. is added 1.2 g (12 mmol) of t-BuOK. The resulting mixture is stirred for 1 hr, and then 0.80 g (3.3 mmol) of I-12 in THF (6 ml) is added. After 2 h, saturated NHCl$_4$ is added followed by EtOAc. The mixture is washed with water and the organic layer is dried with Na$_2$SO$_4$, filtered, concentrated, and purified by silica chromatography (0-10% MeOH in CH$_2$Cl$_2$) to provide a mixture of I-13 and its Z-isomer. The mixture is purified by silica chromatography (0-100% EtOAc in heptane) to provide 500 mg (1.8 mmol) of methyl 3-benzyl-5-[(E)-2-methoxyvinyl]imidazole-4-carboxylate (I-13) as a white solid.

To a stirred solution of compound 2.6 g (9.6 mmol) of I-13 in 30 mL of THF, 10 mL of 2M H$_2$SO$_4$ is added and the reaction mixture is heated to 80° C. for 14 h. The reaction mixture is cooled to 0° C. and aqueous NaOH solution is added to bring the pH to 7. The mixture is extracted with EtOAc and the organic layer is dried over Na$_2$SO$_4$, filtered, concentrated, dissolved in CH$_2$Cl$_2$, and then 1.82 g (48 mmol) of NaBH$_4$ is added. After stirring for 1 h, water is added and the mixture is extracted with CH$_2$Cl$_2$. The organic layer is dried over Na$_2$SO$_4$, concentrated and purified by column chromatography followed by preparative HPLC (30-90% MeCN in water with 0.1% TFA; YMC Triart (150× 19mm)100 to afford the compound I-14 (0.86 g, 35%).

A mixture of 0.20 g (0.75 mmol) of I-14 and 0.14 (0.75 mmol) of p-TsOH in 10 mL of toluene is stirred at 100° C. for 6 h. The reaction mixture is diluted with EtOAc, washed with 1M NaOH, dried over Na$_2$SO$_4$, filtered, concentrated and purified via silica chromatography (0-10% MeOH in CH$_2$Cl$_2$) to give 0.11 g (0.49 mmol) of 3-benzyl-6,7-dihydropyrano[3,4-d]imidazol-4-one (I-15) as a colorless oil.

A mixture of 0.11 g (0.49 mmol) of I-15 and 15 mg of 10% Pd/C in 5 mL of degassed methanol is stirred at overnight. The mixture is filtered and the residue is concentrated to give 68 mg (0.49) of 6,7-dihydro-3H-pyrano[3,4-d]imidazol-4-one (I-16) as a white solid.

Synthesis of 6,6-dimethyl-3,7-dihydropyrano[3,4-d]imidazol-4-one (I-24)

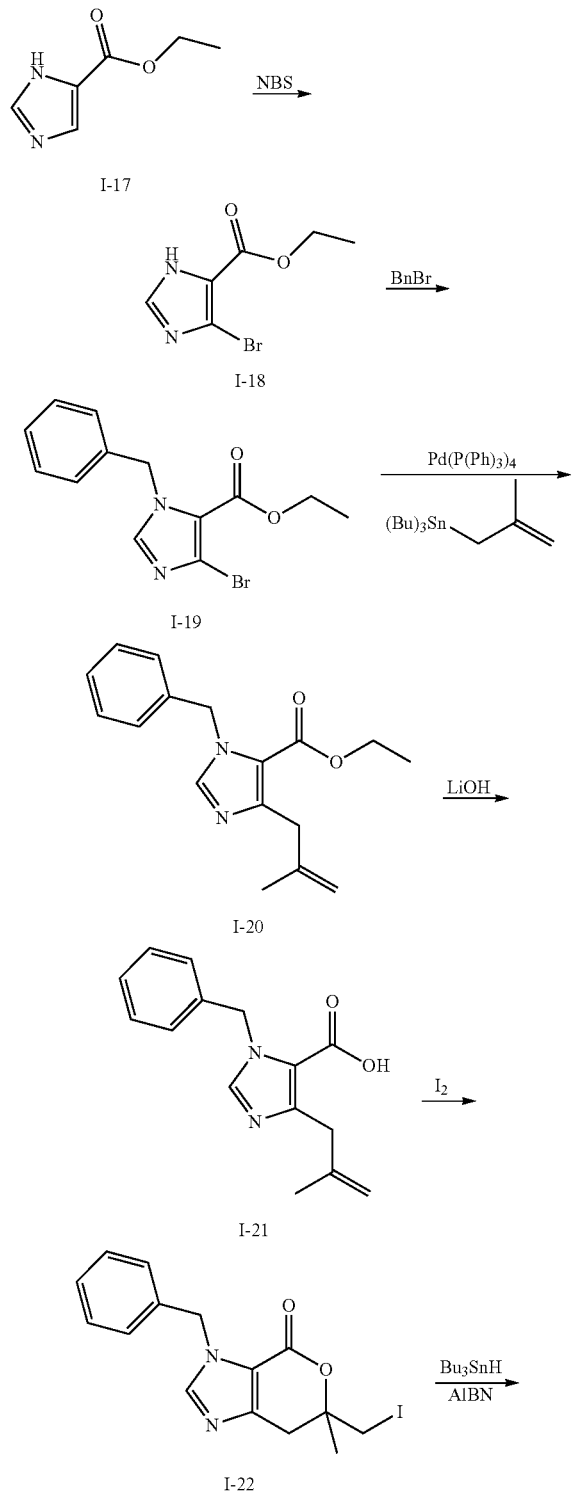

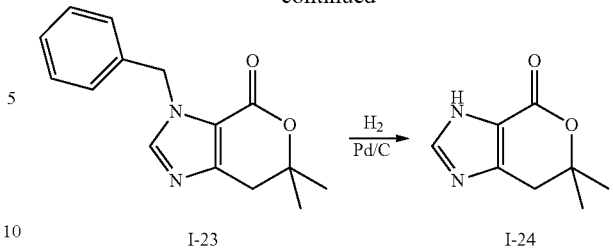

NBS (25 g, 140 mmol) is added to a stirred solution of ethyl 3H-imidazole-4-carboxylate (I-17) in 1.4 L of MeCN. The reaction mixture is stirred for 12 h in the dark, then is concentrated and purified by silica chromatography (0-70% EtOAc in heptane) to provide 17 g (65 mmol) of ethyl 3H-imidazole-4-carboxylate ethyl 4-bromo-1H-imidazole-5-carboxylate (I-18) as a white solid. This material is stirred with 11 g (78 mmol) of $K_2CO_3$ and 8.5 mL (71 mmol) of benzyl bromide in 200 mL of DMF for 12 h. The reaction is diluted with water and extracted with three times with EtOAc. Extracts are combined, washed with brine, dried over $Na_2SO_4$, filtered, concentrated and purified via silica chromatography (0-50% EtOAc in heptane) to provide 9.6 g (31 mmol) of ethyl 3-benzyl-5-bromo-imidazole-4-carboxylate (I-19) as a colorless oil that solidified upon standing.

$Pd(PPh_3)_4$ (0.79 g, 0.69 mmol) and 3.3 mL (14 mmol) of $(Bu)_3Sn(2$-methylallyl) are added to 4.3 g (14 mmol) of I-19 in 30 mL of degassed DMF. The mixture is stirred at 120° C. for 5 h then stirred for 12 h at room temperature. The reaction mixture is partitioned between MeCN and heptane. The layers are separated and the heptane is extracted with MeCN. The combined MeCN extracts are washed with heptane, concentrated, and purified via silica chromatography (0-50% EtOAC in heptane) to provide 2.1 g (7.3 mmol) of ethyl 3-benzyl-5-(2-methylallyl)imidazole-4-carboxylate (I-20) as a yellow oil.

A mixture of 2.7 g (9.7 mmol) of I-20 and 24 mL (48 mmol) of 2M aqueous LiOH and 24 mL of EtOH is stirred for 12 h then concentrated. The resulting residue is taken up in 20 mL $H_2O$ and made acidic (pH 5) by the addition of AcOH. The precipitate is collected by filtration, is washed with $H_2O$ and is dried under a flow of air to provide 2.2 g (8.6 mmol) of 3-benzyl-5-(2-methylallyl)imidazole-4-carboxylic acid (I-21) as a white solid.

To a stirring mixture of 2.2 g (8.6 mmol) of I-21 in 30 mL of THF are added successively 2.9 g (35 mmol) of $NaHCO_3$ and 6.6 g (26 mmol) of $I_2$. The mixture is stirred overnight, aqueous $Na_2S_2O_3$ is added until all red color is gone, and the mixture is extracted three times with EtOAc. The combined extracts are washed with brine, dried ($Na_2SO_4$), filtered, concentrated and purified via silica chromatography (20-80% EtOAc in heptane) to provide 3.0 (7.7 mmol) of 3-benzyl-6-(iodomethyl)-6-methyl-7H-pyrano[3,4-d]imidazol-4-one (I-22) as a yellow oil.

To a solution of 2.4 g (6.3 g) of I-22 in 45 mL of benzene are added 0.1 g (0.6 mmol) of AIBN and 9.4 mL (9.4 mmol) of 1 M $Bu_3SnH$ in cyclohexane dropwise. The solution is heated to reflux for 3 h under an Ar atmosphere. An additional 4.7 mL (4.7 mmol) of $Bu_3SnH$ is added and the mixture is stirred at reflux for 3 h, and then stirred at room temperature for 2 days. The mixture is partitioned between MeCN and heptane and the layers were separated. The MeCN extract is washed twice with heptane and the combined heptane layers are back extracted with MeCN. The combined MeCN are concentration and purified via silica chromatography (25-100% EtOAc in heptane) to provide 1.5 g (5.7 mmol) of 3-benzyl-6,6-dimethyl-7H-pyrano[3,4-d]imidazol-4-one (I-23) as a yellow solid.

A mixture of 1.5 g (5.7 mmol) of I-23 and 0.2 g of 10% Pd/C in 5 mL of EtOH is stirred under an H₂ atmosphere for two days. Addition 0.1 g of 10% Pd/C is added and the mixture is stirred under an H₂ atmosphere for 12 h, then filtered through diatomaceous earth and concentrated to provide 0.94 g (5.6 mmol) of I-24 as a white solid.

Synthesis of 6-(hydroxymethyl)-6-methyl-3,7-dihydropyrano[3,4-d]imidazol-4-one (I-26)

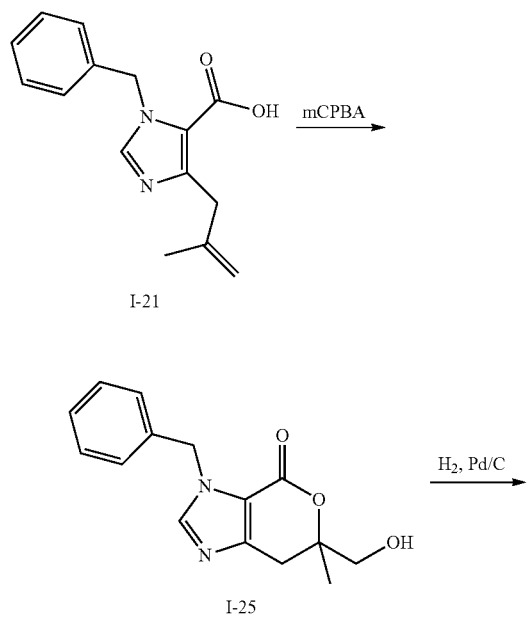

To a mixture of 2.5 g (9.8 mmol) of I-21 in stirring in 10 mL of CH₂Cl₂ is added 3.3 g (15 mmol) of 77% m-CPBA. The mixture is stirred for 12 h, then saturated Na₂S₂O₅ is added followed by water, CH₂Cl₂ and saturated NH₄Cl. The layers are separated and the aqueous wash is extracted twice with CH₂Cl₂. The combined extracts are washed with brine, dried (Na₂SO₄), concentrated and purified by silica chromatography (0-8% MeOH in CH₂Cl₂) to provide 1.8 g (6.6 mmol) of 3-benzyl-6-(hydroxymethyl)-6-methyl-7H-pyrano[3,4-d]imidazol-4-one (I-25) as a white solid.

A mixture of 1.8 g (6.6 mmol) of I-25 and 0.2 g of 10% Pd/C in 50 mL of EtOH and 25 mL of CH₂Cl₂ is stirred under an H₂ atmosphere for 12 h. The mixture is filtered through diatomaceous earth and concentrated to provide 0.97 g of I-26 as a white powder.

Example 1

Synthesis of tert-butyl N-{[3-(3,4-difluorophenyl)-6-methyl-4-oxo-3H,4H,6H,7H-pyrano[3,4-d]imidazol-6-yl]methyl}carbamate (1)

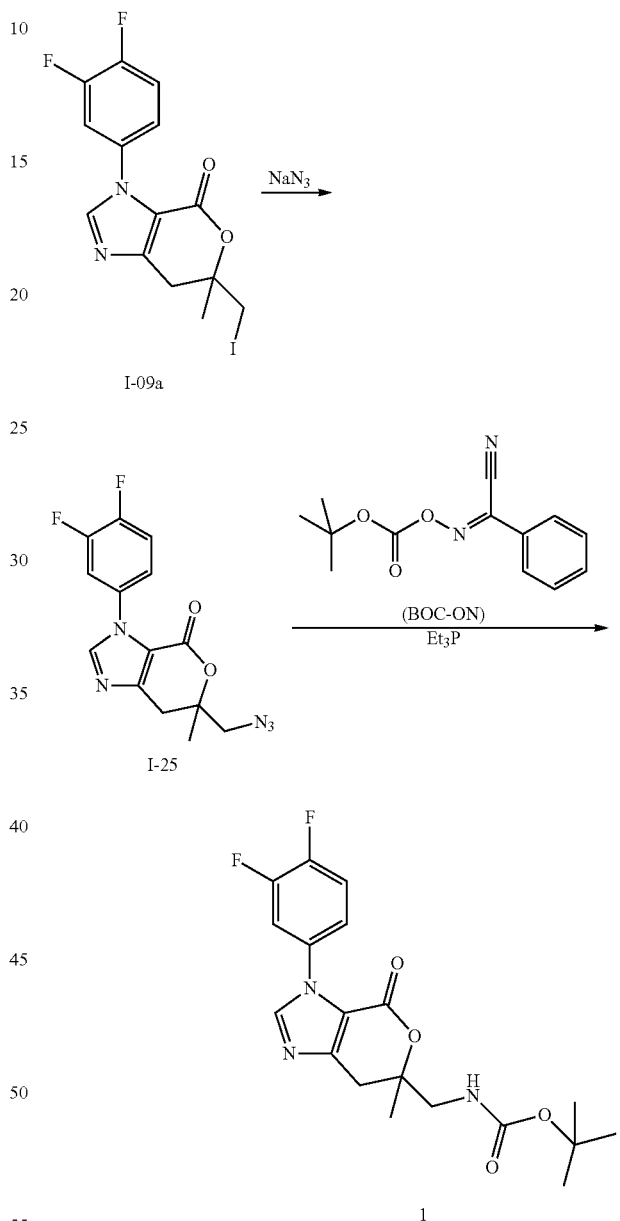

To 0.31 g (0.76 mmol) of I-09a in 5 mL of DMF is added 74 mg (1.1 mmol) of NaN₃. The mixture is heated at 100° C. for 17 h, diluted with 150 mL EtOAc, washed with 2×20 mL of H₂O and once with 20 mL of brine. The extract is dried with MgSO₄, filtered and concentrated. Flash chromatography (0-100% EtOAc/heptanes) provides 112 mg of I-27 that is dissolved in in THF. Triethylphospine (1M in THF; 0.42 mL; 0.42 mmol) and 103 mg (0.42 mmol) of BOC-ON are added and the mixture is stirred for 1 h. The mixture is diluted with 50 mL of EtOAc and washed with 2×20 mL of H₂O and 1×20 mL of brine, then dried with MgSO₄, filtered and concentrated. Preparative TLC (100% EtOAc) provides 58 mg of 1.

Example 2

Synthesis of 3-(3,4-difluorophenyl)-6,6-dimethyl-3H,4H,6H,7H-pyrano[3,4-d]imidazol-4-one (2)

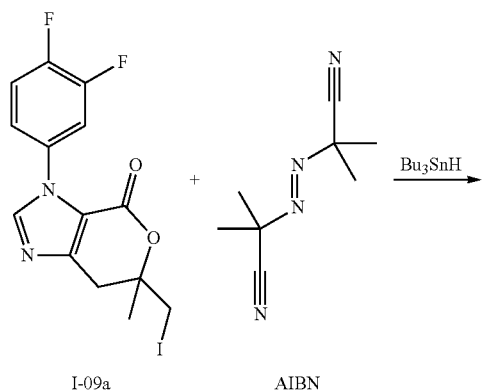

To a solution of 0.41 g (1.0 mmol) of I-09a in benzene are added 16 mg (0.1 mmol) of AIBN and 0.36 g (0.12 mmol) of Bu₃SnH. The solution is heated to reflux for 1.5 h under and Ar atmosphere then cooled to room temperature. The mixture is concentrated and purified by flash chromatography (0-100% EtOAc/heptanes) to give 0.22 g of 2 as a white solid.

The following compounds are prepared from the appropriate iodides I-09e through I-09n in the same manner as 2.

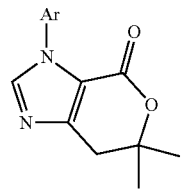

3 from I-09b: Ar=4-cyanophenyl
4 from I-09c: Ar=3,4-dichlorophenyl
5 from I-09d: Ar=1-methyl-3,4-dihydroquinolin-2-one-6-yl
6 from I-09e: Ar=3-chloro-4-cyanophenyl
7 from I-09f: Ar=2-chloro-3-fluorophenyl
8 from I-09g: Ar=2-fluoro-3-chlorophenyl
9 from I-09h: Ar=4-chlorophenyl
10 from I-09i: Ar=3-fluoro-4-cyanophenyl
11 from I-09j: Ar=3-methyl-4-cyanophenyl
12 from I-09m: Ar=3-cyano-4-chlorophenyl
13 from I-09n: Ar=2-methyl-4-cyanophenyl
14 from I-09o: Ar=4-fluorophenyl Example 2

Synthesis of 2-chloro-4-[6-methyl-4-oxo-3H,4H,6H,7H-pyrano[3,4-d]imidazol-3-yl]benzonitrile (15 Enantiomers A & B)

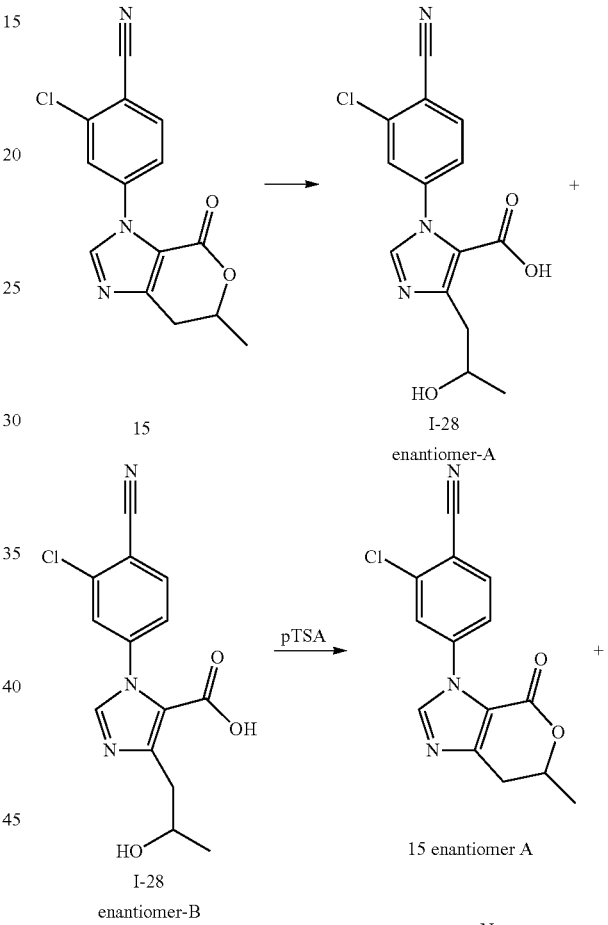

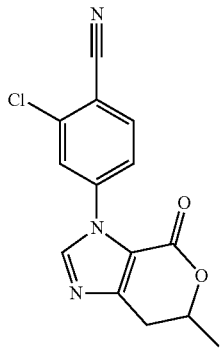

The racemic mixture of 15 is prepared from I-10e in the same manner as 2. Chiral chromatography of 180 mg (Chiral- Pak IA, 30 (1:1:1 MeOH/EtOH/iPA+1% Et₂NH):CO₂, 105 mL/min, 100 bar, 35° C.) delivers I-28 enantiomer A and I-28 enantiomer-B. Each alcohol is separately combined with a catalytic amount of pTSA in 2 mL toluene at 120° C. for 16 h. Each mixture is diluted with 50 mL EtOAc, washed with 2×20 mL of H₂O and once with 20 mL of brine, dried over MgSO₄, filtered and concentrated. Each is purified by preparative TLC (100% EtOAc) to provide 40 mg of 15 enantiomer A and 38 mg of 15 enantiomer B.

Example 3

Synthesis of 4-[6-methyl-4-oxo-3H,4H,6H,7H-pyrano[3,4-d]imidazol-3-yl]benzonitrile (16 Enantiomers A & B)

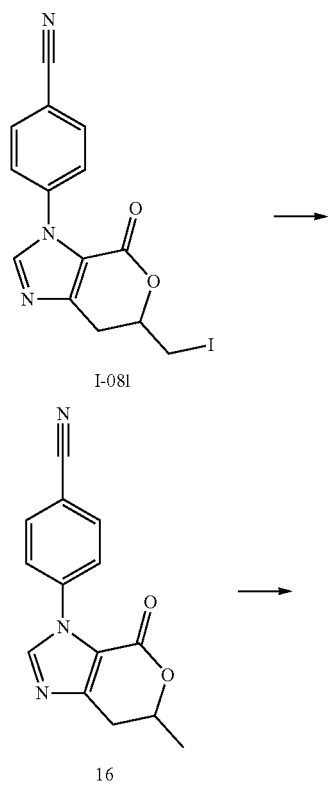

Racemic 16 is prepared from I-10b in the same manner as 2. Chiral chromatography of 58 mg (ChiralPak AD, 55 (MeOH+1% iPrNH₂):CO₂, 80 mL/min, 100 bar, 25° C.) delivers 28 mg of 16 enantiomer A and 23 mg of 16 enantiomer B.

Example 4

Synthesis of 6,6-dimethyl-3-phenyl-3H,4H,6H,7H-pyrano[3,4-d]imidazol-4-one (17)

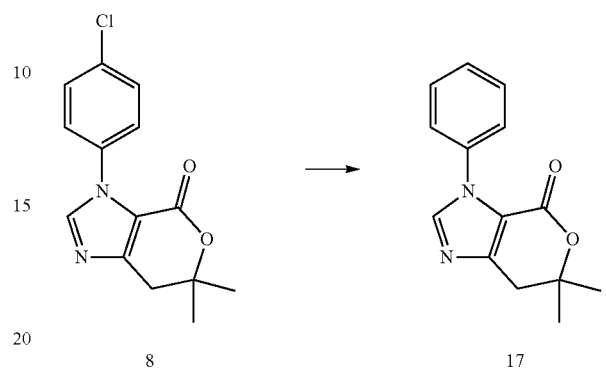

A mixture of 8 (0.10 g; 0.36 mmol) and Pd/C (0.1 g) in EtOAc (50 ml) is stirred at 50° C. under H₂ (50 psi) for 2 days. The mixture is filtered and concentrated to 41 mg of 17 as a white powder.

Example 5

Synthesis of 3-chloro-4-{6,6-dimethyl-4-oxo-3H,4H,6H,7H-pyrano[3,4-d]imidazol-3-yl}benzonitrile (18)

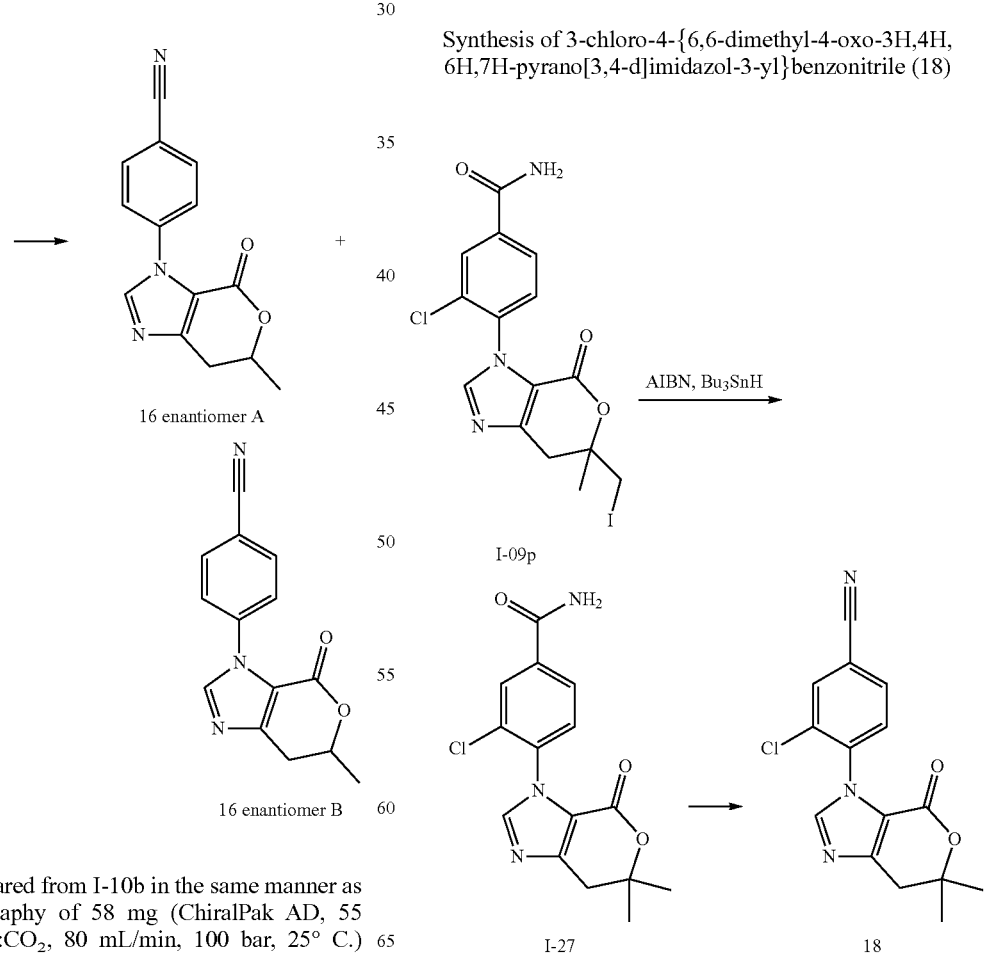

Compound I-29 is prepared from iodide I-09p in the same manner as 2.

To 0.11 g (0.34 mmol) of I-29 in 6 mL of dry dioxane is added 0.54 mL (6.4 mmol) of pyridine and 0.48 mL (0.34 mmol) of trifluoracetic anhydride. The mixture stirred for 2 h then is diluted with 50 mL EtOAc and washed with 20 mL of saturated aqueous NH₄Cl, twice each with 20 mL of H₂O and once with 20 mL of brine. The organic phase is dried with MgSO₄, filtered and concentrated. Preparative TLC (100% EtOAc) provides 55 mg of 18.

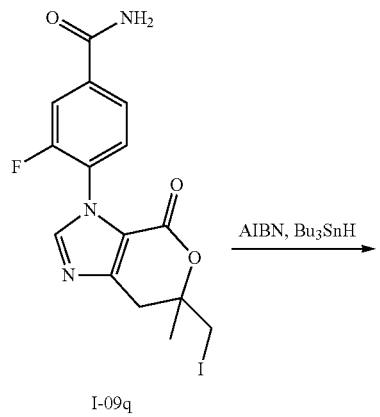

I-09q

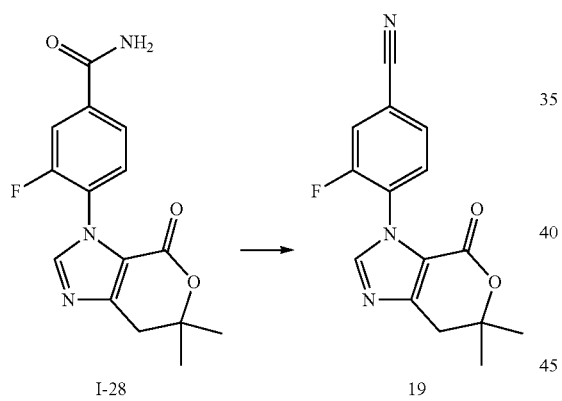

I-28      19

19 is prepared from I-09q in the same manner as 18.

Example 6

Synthesis of 3-(4-chlorophenyl)-3H,4H,6H,7H-pyrano[3,4-d]imidazol-4-one (20)

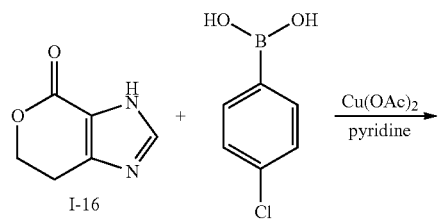

I-16

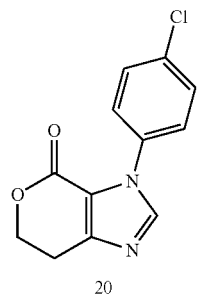

20

A mixture of 30 mg (0.22 mmol) of I-16, 51 mg (0.33 mmol) of 4-chlorophenylboronic acid, 63 mg (0.35 mmol) of Cu(OAc)₂, 0.07 mL (0.9 mmol) of pyridine in 2 mL of CH₂Cl₂ is stirred for 12 h. The mixture is filtered through a short pad of silica gel then concentrated and purified by preparative TLC (4% MeOH in CH₂Cl₂) to give 7 mg (0.03 mmol) of 20 as a white solid as well as 3 mg of 1-(4-chlorophenyl)-3H,4H,6H,7H-pyrano[3,4-d]imidazol-4-one.

Compounds 21-24 are prepared from I-16 and the appropriate boronic acids in the same manner as 20.

21-24

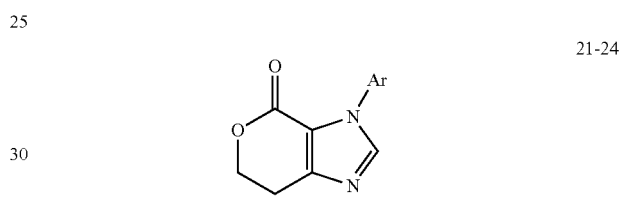

21 from 4-cyanophenylboronic acid
22 from 3-chloro-4-cyanophenylboronic acid
23 from 3,4-dichlorophenylboronic acid
24 from 3,4-difluorophenylboronic acid Example 7

Synthesis of 3-(2,3-dihydro-1H-inden-2-yl)-3H,4H,6H,7H-pyrano[3,4-d]imidazol-4-one (25)

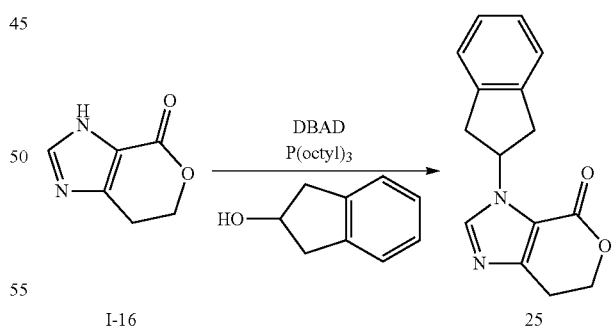

I-16      25

To a mixture of 50 mg (0.36 mmol) of I-16, 0.17 g (0.47 mmol) of trioctylphosphine, 50 mg (0.37 mmol) of indane-2-ol in 5 mL of THF at 0° C., 110 mg (0.47 mmol) of di-tert-butyl azodicarboxylate (DBAD) is added over 5 min. After stirring for 12 h, the mixture is concentrated and purified by preparative reverse-phase HPLC (5-95% MeCN in water) to provide 57 mg (0.22 mmol) of 25 as a white solid.

The following compounds are prepared from the appropriate alcohol and the appropriate imidazole in the same manner as 25.

3-(2,3-dihydro-1H-inden-2-yl)-6,6-dimethyl-3H,4H,6H,
7H-pyrano[3,4-d]imidazol-4-one (26) from indano-2-ol
and I-24.

3-(2,3-dihydro-1H-inden-2-yl)-6-(hydroxymethyl)-6-methyl-3H,4H,6H,7H-pyrano[3,4-d]imidazol-4-one (27)
from indan-2-ol and I-26.

trans-4-(6,6-Dimethyl-4-oxo-6,7-dihydro-4H-pyrano[3,
4-d]imidazol-3-yl)-cyclohexanecarbonitrile (28) from
cis-4-hydroxycyclohexanecarbonitrile and I-24.

Example 8

Synthesis of 2-chloro-4-[(6R)-6-(hydroxymethyl)-6-methyl-4-oxo-3H,4H,6H,7H-pyrano[3,4-d]imidazol-3-yl]benzonitrile (29 Enantiomer A) and 2-chloro-4-[(6S)-6-(hydroxymethyl)-6-methyl-4-oxo-3H,4H,6H,7H-pyrano[3,4-d]imidazol-3-yl]benzonitrile (29 Enantiomer B)

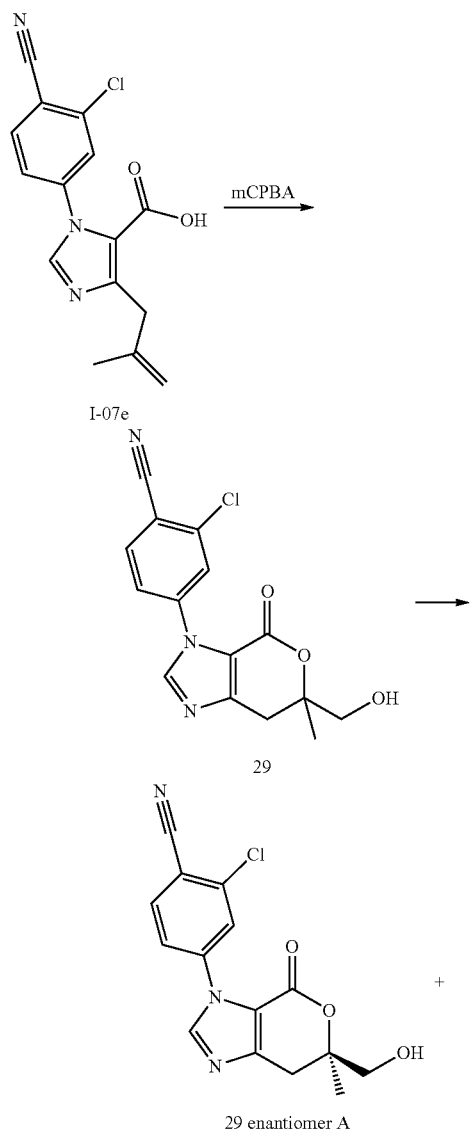

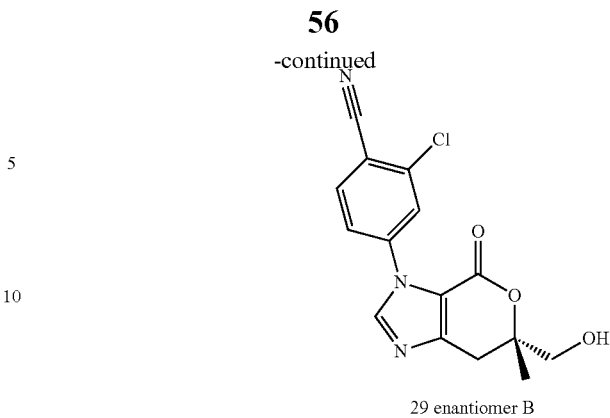

29 enantiomer B

A mixture of 0.50 g (1.7 mmol) of I-07e and 0.56 g (2.5 mmol) of 77% m-CPBA (m-chloroperoxybenzoic acid) in 10 mL of $CH_2Cl_2$ is stirred for 16 h. EtOAc (200 mL) and 20 mL of 10% $Na_2SO_3$ are added. The mixture is washed twice with 50 mL of $NaHCO_3$ and the washes are extracted with 50 mL of $CH_2Cl_2$. The organic extracts are combined, dried with MgSO4, filtered and concentrated to give 507 mg of racemic 29 as a pale yellow solid. Chiral chromatography of 507 mg (LUX 5u Cellulose 4, 28% EtOH:$CO_2$, 80 g/min, 120 bar, 40° C.) delivers 238 mg of 29 enantiomer A and 230 mg of 29 enantiomer B. The absolute stereochemistry for compounds 29A and 29B were determined by high resolution single crystal X-ray crystallography structure determination and careful examination of the Flack parameter on the refined structures (H. D. Flack and G. Bernardinelli, 2008, Chirality, 20, 681-690).

The following compounds are prepared from the appropriate olefin I-07c and n in the same manner as 29 enantiomers A & B.

3-(3,4-dichlorophenyl)-6-(hydroxymethyl)-6-methyl-3H,4H,6H,7H-pyrano[3,4-d]imidazol-4-one (30 Enantiomers A & B) from I-07c. (RegisPack, 25% (EtOH+1% iPrNH$_2$):CO$_2$, 80 mL/min, 100 bar, 25° C.)

4-[6-(hydroxymethyl)-6-methyl-4-oxo-3H,4H,6H,7H-pyrano[3,4-d]imidazol-3-yl]-3-methylbenzonitrile (31 Enantiomers A & B) from I-07n. (LUX 5u Cellulose 4, 25% EtOH:CO$_2$, 90 g/min, 120 bar, 40° C.)

Example 8a

Synthesis of [3-(3-chloro-4-cyanophenyl)-6-methyl-4-oxo-3H,4H,6H,7H-pyrano[3,4-d]imidazol-6-yl]methyl acetate (32)

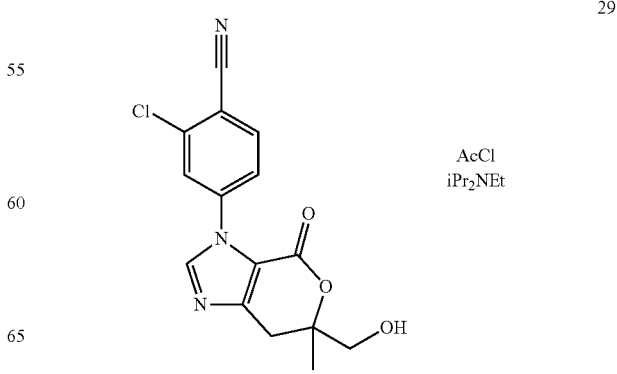

-continued

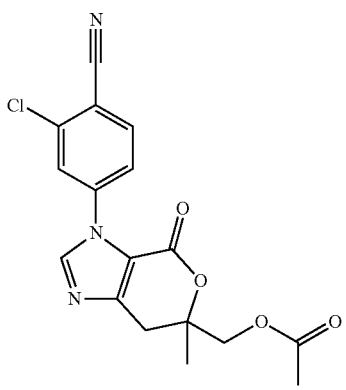

32

To 50 mg (0.16 mmol) of racemic 29 in 5 mL of CH$_2$Cl$_2$ at 4° C. is added 0.18 mL (0.18 mmol) of 1 M AcCl in CH$_2$Cl$_2$ followed by 0.04 mL (0.2 mmol) of iPr$_2$NEt. After stirring for 16 h an additional 0.18 mL (0.18 mmol) of 1 M AcCl solution is added and the mixture stirred for 72 h. EtOAc is added (50 mL), and the mixture is washed with 20 mL of saturated NH$_4$Cl, twice with 20 mL of water, and once with 20 mL of brine. The organic phase is dried with MgSO$_4$, filtered, concentrated, and purified by preparative TLC (100% EtOAc) to give 43 mg (0.12 mmol) of 32.

Example 9

Synthesis of 2-chloro-4-[6-(hydroxymethyl)-4-oxo-3H,4H,6H,7H-pyrano[3,4-d]imidazol-3-yl]benzonitrile (33 Enantiomers A & B)

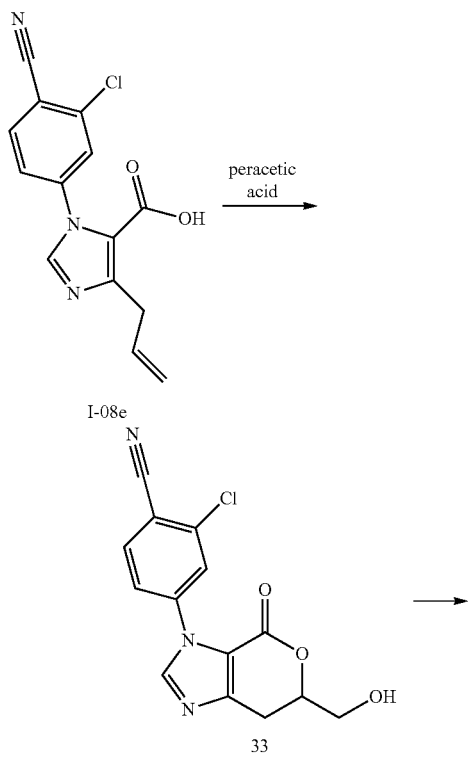

-continued

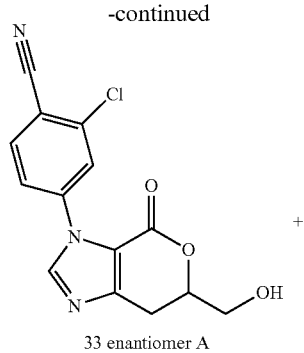

33 enantiomer A

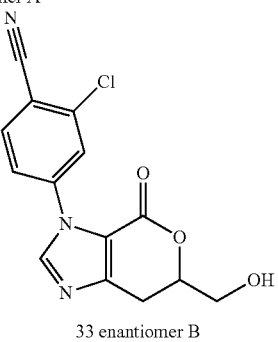

33 enantiomer B

To 0.25 g (0.87 mmol) of I-8e in 4 mL of acetone is added 1.1 mL of 32% peracetic acid (5.2 mmol). The mixture is heated at 50° C. for 24 h, then is concentrated and purified by silica chromatography (0-10% MeOH in CH$_2$Cl$_2$) to give 110 mg (0.37 mmol) of racemic 33. Chiral chromatography of 103 mg (LUX 5u Cellulose 4, 35% (1:1:1 MeOH/EtOH/iPA):CO$_2$, 80 g/min, 120 bar, 35° C.) followed by preparative TLC (5% MeOH in CH$_2$Cl$_2$) delivers 48 mg (0.16 mmol) of 33 enantiomer A and 33 mg (0.11 mmol) of 33 enantiomer B.

The following compounds are prepared from the appropriate olefin I-07 or I-08 in the same manner as 33 enantiomers A & B.

3-(2-chloro-3-fluorophenyl)-6-(hydroxymethyl)-6-methyl-3H,4H,6H,7H-pyrano[3,4-d]imidazol-4-one (34 enantiomers A & B) from I-07g. (RegisPack, 20% (1:1:1 MeOH/EtOH/iPA):CO$_2$, 135 mL/min, 120 bar, 35° C.)

3-(3-chloro-2-fluorophenyl)-6-(hydroxymethyl)-6-methyl-3H,4H,6H,7H-pyrano[3,4-d]imidazol-4-one (35 enantiomers A & B) from I-07f. (ChiralPak IA, 25% (1:1:1 MeOH/EtOH/iPA):CO$_2$, 120 g/min, 120 bar, 35° C.)

3-(4-chlorophenyl)-6-(hydroxymethyl)-3H,4H,6H,7H-pyrano[3,4-d]imidazol-4-one (36) from I-8h without chiral resolution.

4-[6-(hydroxymethyl)-6-methyl-4-oxo-3H,4H,6H,7H-pyrano[3,4-d]imidazol-3-yl]benzonitrile (37) from I-07b without chiral resolution.

3-(4-chlorophenyl)-6-(hydroxymethyl)-6-methyl-3H,4H,6H,7H-pyrano[3,4-d]imidazol-4-one (38 enantiomers A & B) from I-07h. (LUX 5u Cellulose 4, 20% (1:1:1 MeOH/EtOH/iPA+1% Et$_2$NH):CO$_2$, 80 mL/min, 120 bar, 40° C.)

4-[6-(hydroxymethyl)-6-methyl-4-oxo-3H,4H,6H,7H-pyrano[3,4-d]imidazol-3-yl]-2-methylbenzonitrile (39 enantiomers A & B) from I-07j. (LUX 5u Cellulose 4, 25% (1:1:1 MeOH/EtOH/iPA):CO$_2$, 80 g/min, 120 bar, 35° C.)

6-[6-(hydroxymethyl)-6-methyl-4-oxo-3H,4H,6H,7H-pyrano[3,4-d]imidazol-3-yl]-1-methyl-1,2,3,4-tetrahydroquinolin-2-one (40 enantiomers A & B) from I-07d. (Lux Amylose-2, 25% (75:25 MeO/iPA):CO$_2$, 90 g/min, 120 bar, 40° C.)

Example 10

Synthesis of 3-(3,4-dichlorophenyl)-6-methyl-3H,4H,6H,7H-pyrano[3,4-d]imidazol-4-one (41)

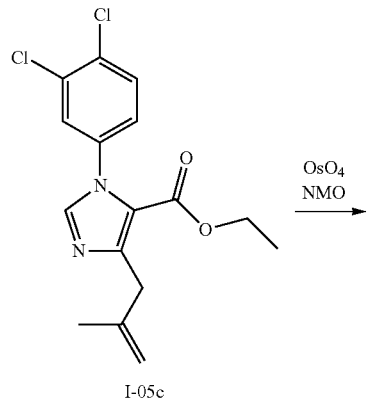

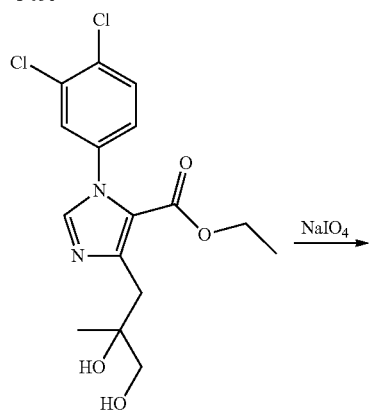

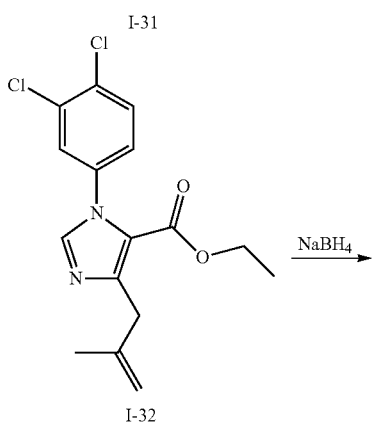

To a mixture of 0.52 g (1.5 mmol) of I-05c in 4 mL of 50% acetone and water is added 2.5 g (0.24 mmol) of 2.5% OsO$_4$ in t-butanol, and 0.27 g (2.3 mmol) of 4-methylmorpholine N-oxide (NMO). After 2 h, saturated sodium thiosulfate is added, the mixture is concentrated and then is suspended in water and extracted with EtOAc (50 mL×3). The organic phase is dried over MgSO$_4$, filtered, concentrated, and purified by silica chromatography (0-10% MeOH in CH$_2$Cl$_2$) to give 0.41 g (1.1 mmol) of 3-(3,4-dichloro-phenyl)-5-(2,3-dihydroxy-2-methyl-propyl)-3H-imidazole-4-carboxylic acid ethyl ester (I-31).

To 0.37 g (1.0 mmol) of I-31 in 10 mL of 1:1 THF/water is added 0.32 g (1.5 mmol) of NaIO$_4$. After stirring for 2 h, 50 mL of EtOAc is added. The mixture is washed with twice with 20 mL of water and once with 20 mL of brine. The organic phase is dried with MgSO$_4$, filtered, and concentrated to provide 0.33 g (0.96 mmol) of 3-(3,4-dichloro-phenyl)-5-(2-oxo-propyl)-3H-imidazole-4-carboxylic acid ethyl ester (I-32) that is stirred in 5 mL of THF. NaBH$_4$ (73 mg, 1.9 mmol) is added. After stirring for 3.5 h, 50 mL of EtOAc is added. The mixture is washed with 20 mL of saturated NH$_4$Cl, twice with 20 mL of water and once with 20 mL of brine. The organic phase is dried over MgSO$_4$, filtered, concentrated and purified by silica chromatography (0-100% EtOAc in heptanes) to give 0.10 g (0.34 mmol) of 41.

Example 11

Synthesis of 3-(2,3-dihydro-benzofuran-5-yl)-6-hydroxymethyl-6-methyl-6,7-dihydro-3H-pyrano[3,4-d]imidazol-4-one (42 Enantiomers A and B)

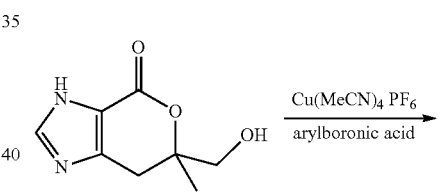

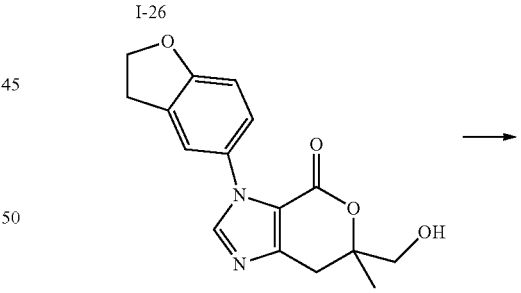

+

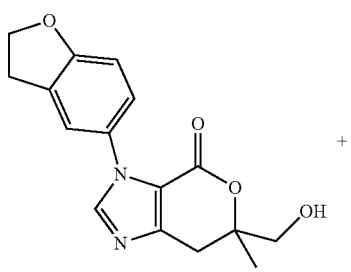

enantiomer A

-continued

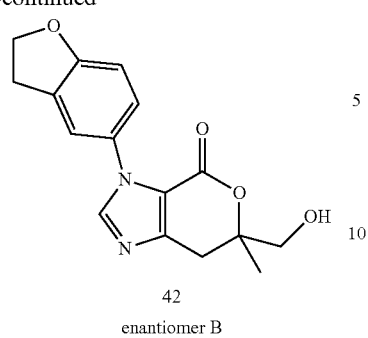

42
enantiomer B

A mixture of 0.15 g (0.82 mmol) of I-26, 0.15 g (0.91 mmol) of 2,3-dihydro-1-benzofuran-5-ylboronic acid 92 mg (0.25 mmol) of $Cu(MeCN)_4PF_6$ in 6 mL of MeOH is vigorously stirred for 12 h. The mixture is filtered through diatomaceous earth, concentrated and purified via column chromatography (0-7% MeOH in $CH_2Cl_2$) to provide 60 mg (0.20 mmol) of 42. Chiral chromatography (LUX 5u Cellulose 3 Prep, 10% (1:1 MeOH/EtOH):$CO_2$, 88 g/min, 120 bar, 40° C.) delivers 30 mg (0.10 mmol) each of 42 enantiomer A and 42 enantiomer B.

Example 12

Synthesis of 2-chloro-4-(6-formyl-6-methyl-4-oxo-6,7-dihydro-4H-pyrano[3,4-d]imidazol-3-yl)-benzonitrile (43)

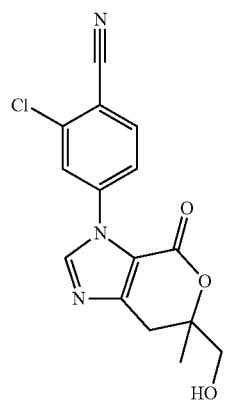

29

+

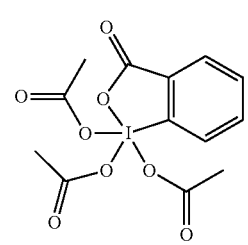

Dess-Martin
Periodinane

-continued

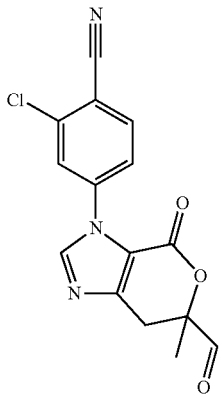

43

To a stirred mixture of 0.50 g (1.6 mmol) of 29 in $CH_2Cl_2$ is added 0.73 g (1.7 mmol) of Dess-Martin periodinane. After reaction mixture is stirred for 2 h, a mixture of $NaHCO_3$/$Na_2S_2O_3$ (1:1 saturated aqueous) is added. The organic phase is dried, filtered, and concentrated to provide 0.30 g (0.95 mmol) of 43.

Example 13

Synthesis of 3-(3-chloro-4-cyano-phenyl)-6-methyl-4-oxo-3,4,6,7-tetrahydro-pyrano[3,4-d]imidazole-6-carboxylic acid (44)

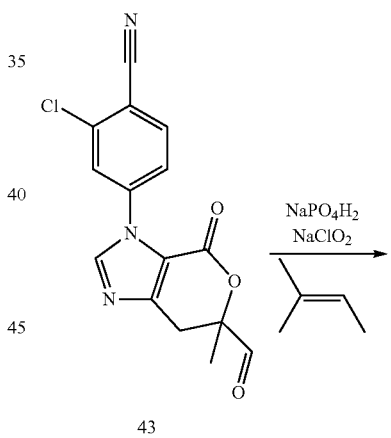

43

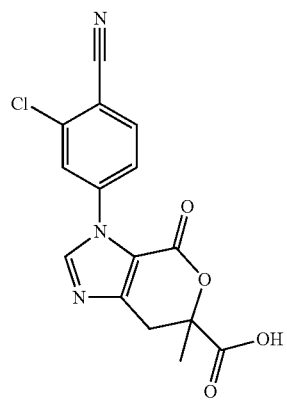

44

To 50 mg (0.16 mmol) of 43 in each of t-BuOH H₂O is added 0.84 mL (7.9 mmol) of 2-methyl-but-2-ene, 71 mg (0.79 mmol) of NaClO₂ and 76 mg (0.63 mmol) of NaH₂PO₄. The mixture stirred for 1 h, and then 20 mL of saturated NH₄Cl is added. The mixture is extracted three times with 20 mL of EtOAc, and the extract is dried with MgSO₄, filtered, and concentrated to provide 46 mg (0.14 mmol) of 44.

Example 14

Synthesis of 3-(3-chloro-4-cyano-phenyl)-6-methyl-4-oxo-3,4,6,7-tetrahydro-pyrano[3,4-d]imidazole-6-carboxylic acid methyl ester (45)

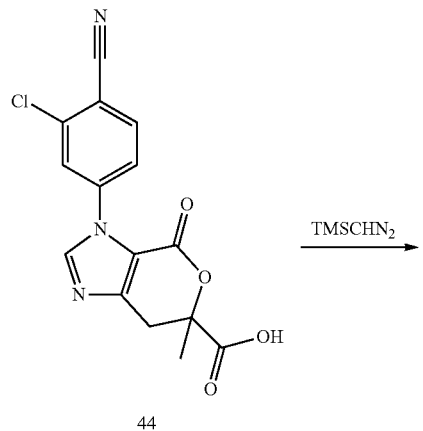

44

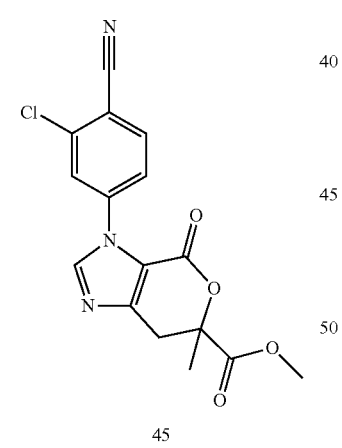

45

To 50 mg (0.15 mmol) of 44 in 2 mL of a 1:1 CH₂Cl₂/MeOH is added 0.07 mL (0.14 mmol) of 2 M trimethylsilyl diazomethane in hexanes. After stirring for 1 h another 0.07 mL (0.14 mmol) of 2M trimethylsilyl diazomethane is added. The mixture is stirred for 1 h, concentrated, dissolved in 50 mL of EtOAc, and washed with twice with 20 mL of H₂O and once with 20 mL of brine. The organic phase is dried with MgSO₄, filtered, and concentrated to give 21 mg (0.06 mmol) of 45.

Example 15

Synthesis of 3-(3-chloro-4-cyano-phenyl)-6-methyl-4-oxo-3,4,6,7-tetrahydro-pyrano[3,4-d]imidazole-6-carboxylic acid dimethylamide (46)

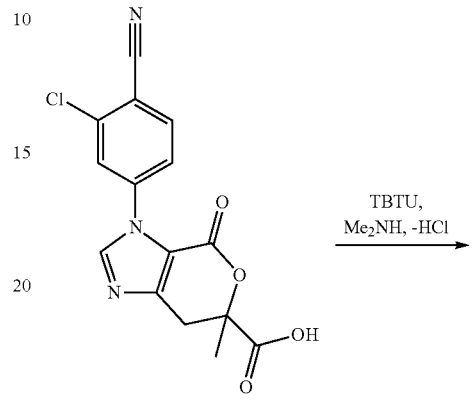

44

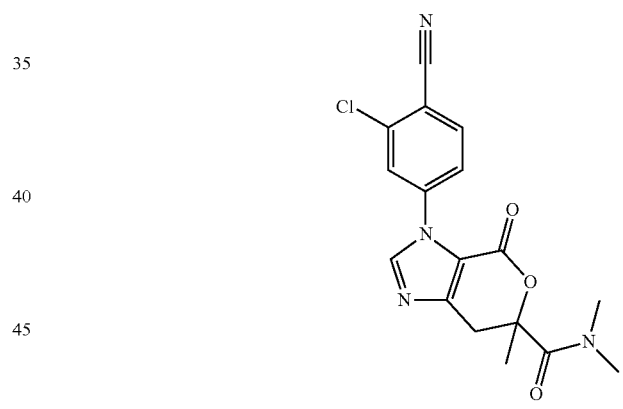

46

To 50 mg (0.15 mmol) of 44 in 2 mL of DMF is added 58 mg (0.18 mmol) of TBTU, 15 mg (0.18 mmol) of dimethylamine hydrochloride and 0.03 mL (0.2 mmol) of iPr₂NEt. The mixture is stirred for 48 h, diluted with 50 mL of EtOAc, and washed twice with 20 mL of H₂O and once with 20 mL of brine. The organic phase is dried with MgSO₄, filtered, concentrated, and purified twice by preparative TLC (100% EtOAc) to give 22 mg (0.06 mmol) of 46.

LCMS data are measured using the methods set forth in Table 2. Data for compounds in Table 1 are shown in Table 3. Compounds that were separated into their enantiomers are shown by separate entries for enantiomer A and enantiomer B.

TABLE 2

LC/MS Methods

| Method | Mobile Phase A | Mobile Phase B | Gradient | Flow (mL/min.) | Column |
|---|---|---|---|---|---|
| A | 95% Water 5% MeCN + 0.05% Formic Acid | MeCN + 0.05% Formic Acid | 90% A to 100% B in 1.19 min. hold at 100% B to 1.70 min. | 0.8 | BEH 2.1 × 50 mm C18, 1.7 µm particle diameter |
| B | 95% Water 5% MeCN + 0.05% Formic Acid | MeCN + 0.05% Formic Acid | 90% A to 100% B in 4.45 min. hold at 100% B to 4.58 min. | 0.8 | BEH 2.1 × 50 mm C18, 1.7 µm particle diameter |

TABLE 3

LC/MS Data

| Compound No. | $(M + H)^+$ | HPLC method | HPLC Retention Time (min) |
|---|---|---|---|
| 1 | 394.2 | A | 0.98 |
| 2 | 279.1 | A | 0.76 |
| 3 | 267.9 | A | 0.64 |
| 4 | 311.0 | A | 1.1 |
| 5 | 326.2 | A | 0.61 |
| 6 | 302.1 | B | 1.3 |
| 7 | 295.1 | A | 0.87 |
| 8 | 295.1 | A | 0.83 |
| 9 | 277.0 | A | 0.74 |
| 10 | 286.1 | A | 0.67 |
| 11 | 282.3 | A | 0.67 |
| 12 | 301.9 | A | 0.76 |
| 13 | 281.9 | A | 0.7 |
| 14 | 261.4 | A | 0.67 |
| 15 A | 287.9 | A | 0.68 |
| 15 B | 287.9 | A | 0.68 |
| 16 A | 253.9 | A | 0.58 |
| 16 B | 253.9 | A | 0.58 |
| 17 | 243.1 | A | 0.69 |
| 18 | 302.1 | A | 0.68 |
| 19 | 286.1 | A | 0.64 |
| 20 | 249.0 | A | 0.65 |
| 21 | 240.0 | A | 0.53 |
| 22 | 273.9 | A | 0.61 |
| 23 | 282.9 | A | 0.75 |
| 24 | 251.1 | A | 0.65 |
| 25 | 254.8 | A | 0.70 |
| 26 | 283.1 | A | 0.8 |
| 27 | 299.1 | A | 0.65 |
| 28 | 274.0 | A | 0.62 |
| 29 A | 318.1 | A | 0.58 |
| 29 B | 317.9 | A | 0.54 |
| 30 A | 326.9 | A | 0.69 |
| 30 B | 326.9 | A | 0.68 |
| 31 A | 297.9 | A | 0.53 |
| 31 B | 297.9 | A | 0.53 |
| 32 | 360.1 | A | 0.73 |
| 33 A | 304.4 | A | 0.53 |
| 33 B | 304.4 | A | 0.53 |
| 34 A | 311.0 | A | 0.61 |
| 34 B | 310.6 | A | 0.61 |
| 35 A | 311.0 | A | 0.65 |
| 35 B | 311.0 | A | 0.65 |
| 36 | 279.1 | A | 0.58 |
| 37 | 284.2 | A | 0.49 |
| 38 A | 293.4 | A | 0.63 |
| 38 B | 293.5 | A | 0.63 |
| 39 A | 298.1 | A | 0.55 |
| 39 B | 298.1 | A | 0.55 |
| 40 A | 342.0 | B | 1.32 |
| 40 B | 342.0 | B | 1.32 |
| 41 | 297.0 | A | 0.80 |
| 42 A | 301.0 | A | 0.56 |
| 42 B | 301.0 | A | 0.56 |
| 43 | 348 $(M + MeOH)^+$ | A | 0.64 |
| 44 | 332.0 | A | 0.66 |
| 45 | 346.1 | A | 0.75 |
| 46 | 359.0 | A | 0.70 |

ASSESSMENT OF BIOLOGICAL ACTIVITY

Preparation of Cynomolgus Adrenal Mitochondria.

The aldosterone synthase and cortisol synthase inhibition assays employ cynomolgus adrenal gland mitochondria as the source of aldosterone synthase (CYP11B2) and cortisol synthase (CYP11B1). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use. One unit of CYP11B2 and CYP11B1 activity in these preparations is defined as the amount of enzyme that generates 1 pmol of product in one hour under the conditions described.

Inhibition of Aldosterone Synthase

The compounds of the invention may be evaluated for aldosterone synthase inhibition by the following assay:

Assays are performed in 96-well format in a final volume of 60 microL/well, containing 100 mM potassium phosphate, pH 7.4, 1% (v/v) DMSO, and additionally, 2 µM of corticosterone and 50 units of CYP11B2 activity. Reactions are started by the addition of NADPH to 1 mM and allowed to proceed for 90 minutes at 37° C. Reactions are terminated by the addition of 60 µL of MeCN containing an internal standard for mass spectrometry. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity (IC$_{50}$) determined using the XLFit curve-fitting program using a 4-parameter logistic model.

Inhibition of Cortisol Synthesis

Assays are performed as for aldosterone synthase except for the use of 150 units of CYP11B1, 11-deoxycortisol as substrate and cortisol measured as product.

Inhibition of CYP17A1

Compounds of the invention may also be evaluated for inhibition of CYP17A1 via the following assay:

Assays are performed in a 96-well format with a final volume of 40 μL/well containing 100 mM potassium phosphate buffer, pH 7.4, 1% DMSO (v/v), and additionally 150 nM progesterone and 0.025 mg/mL of rhCYP17A1 (purchased from Cypex). Reactions are started by the addition of NADPH to 1 mM and allowed to proceed for 15 minutes at 37° C. Reactions are terminated by the addition of 40 μL of MeCN containing an internal standard for mass spectrometry. The plates are centrifuged at 3000 rpm for 5 min and the reaction product 17-α-hydroxyprogesterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity (IC$_{50}$) determined using a 4-parameter logistic model.

Inhibition of CYP19A1

Compounds of this invention may also be evaluated for inhibition of CYP19A1 (Kragie, L. et al., 2002, Endocrine Research, 28 (3), 129-140).

Representative compounds of the present invention were tested for activity in the above assays. Preferred compounds have an IC$_{50}$<1,000 nM and more preferred compounds have an IC$_{50}$<100 nM in the aldosterone synthase inhibition assay. Preferred compounds have at least 100-fold selectivity for aldosterone synthase inhibition over cortisol synthase (CYP11B1) inhibition and at least 500-fold over CYP17A1 and CYP19A1. As examples, data for representative compounds from Table 1 are shown in Table 4. Data for individual enantiomers are indicated by separate entries for enantiomers A and B

TABLE 4

| Biological Data | | | | |
|---|---|---|---|---|
| Compound No. | Aldosterone Inhibition IC$_{50}$ (nM) | Cortisol Inhibition IC$_{50}$ (μM) | CYP17A1 IC$_{50}$ (μM) | CYP19A1 IC$_{50}$ (μM) |
| 1 | 55 | 2.3 | | |
| 2 | 91 | 3.4 | >20 | >20 |
| 3 | 35 | 8.7 | >20 | >20 |
| 4 | 8.4 | 1.2 | | |
| 5 | 110 | 40 | >20 | >20 |
| 6 | 5.3 | 2.5 | >20 | >20 |
| 7 | 50 | 6.8 | | |
| 8 | 35 | 5.3 | >20 | >20 |
| 9 | 32 | 2.4 | >20 | >20 |
| 10 | 43 | 4.2 | >20 | >20 |
| 11 | 4.9 | 0.59 | >20 | >20 |
| 12 | 290 | 24 | | |
| 13 | 6.3 | 2.2 | >20 | >20 |
| 14 | 130 | 13 | | |
| 15A | 7.5 | 3.4 | | |
| 15B | 12 | 6.4 | | |

TABLE 4-continued

| Biological Data | | | | |
|---|---|---|---|---|
| Compound No. | Aldosterone Inhibition IC$_{50}$ (nM) | Cortisol Inhibition IC$_{50}$ (μM) | CYP17A1 IC$_{50}$ (μM) | CYP19A1 IC$_{50}$ (μM) |
| 16A | 100 | 26 | >20 | >20 |
| 16B | 160 | 35 | >20 | >20 |
| 17 | 390 | 61 | | |
| 18 | 17 | 4.1 | >20 | >20 |
| 19 | 46 | 7.1 | >20 | >20 |
| 20 | 470 | 65 | | |
| 21 | 420 | 82 | | |
| 22 | 25 | 18 | | |
| 23 | 14 | 10 | | |
| 24 | 440 | 20 | | |
| 25 | 500 | >30 | | |
| 26 | 64 | 25 | | |
| 27 | 220 | >30 | | |
| 28 | 75 | 16 | >20 | >20 |
| 29A | 16 | 4.7 | >20 | >20 |
| 29B | 48 | 23 | >20 | >20 |
| 30A | 28 | 9.0 | >20 | >20 |
| 30B | 31 | 5.2 | >20 | >20 |
| 31A | 23 | 3.6 | >20 | >20 |
| 31B | 210 | 24 | >20 | >20 |
| 32 | 36 | 6.5 | | |
| 33A | 89 | 45 | >20 | >20 |
| 33B | 27 | 14 | >20 | >20 |
| 34A | 870 | >30 | | |
| 34B | 120 | 19 | >20 | >20 |
| 35A | 70 | 24 | 15 | >20 |
| 35B | 620 | >30 | | |
| 36 | 540 | >100 | | |
| 37 | 210 | 34 | | |
| 38A | 120 | 19 | | |
| 38B | 390 | 36 | | |
| 39A | 11 | 1.4 | >20 | >20 |
| 39B | 13 | 8.6 | >20 | >20 |
| 40A | 160 | >30 | | |
| 40B | 460 | >30 | | |
| 41 | 8.6 | 6.0 | | |
| 42A | 210 | >30 | | |
| 42B | 76 | >30 | >20 | >20 |
| 43 | 540 | >30 | >20 | >20 |
| 44 | 670 | >30 | >20 | >20 |
| 45 | 28 | 1.1 | | |
| 46 | 89 | 13 | | |

METHODS OF THERAPEUTIC USE

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic kidney disease including diabetic nephropathy;

Non-diabetic kidney disease including glomerulosclerosis, glomerulonephritis, IGA nephropathy, nephritic syndrome and focal segmental glomerulosclerosis (FSGS);

Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;

Adrenal hyperplasia and primary and secondary hyperaldosteronism.

These disorders have been well characterized in man, but also exist with a similar etiology in other mammals, and can be treated by pharmaceutical compositions of the present invention.

Accordingly, a compound of formula I according to any of the embodiments described herein or a pharmaceutically acceptable salt thereof may be used for the preparation of a medicament for treating a disease or disorder mediated by aldosterone synthase, including diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition.

Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I

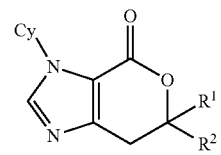

wherein:

Cy is a monocyclic or bicyclic ring system selected from $C_{3-10}$cycloalkyl, heterocyclyl, aryl and heteroaryl,
   wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl$)_2$, —$NH(C_{1-3}$-alkyl), —$NHCOC_{1-3}$-alkyl, —$C(O)C_{1-3}$-alkyl, —$C(O)OC_{1-3}$alkyl, hydroxy$C_{1-3}$alkyl, or heteroaryl; and $R^1$ and $R^2$ are independently selected from H, $C_{1-3}$alkyl, hydroxy$C_{1-3}$alkyl, —$CH_2NHC(O)OC_{1-4}$alkyl, —$CH_2OC(O)C_{1-4}$alkyl, —$C(O)OC_{1-4}$-alkyl, —$C(O)H$, —COOH, —$C(O)NHC_{1-4}$-alkyl and $C(O)N(C_{1-4}$-alkyl$)_2$; or $R^1$ and $R^2$ taken together form a $C_{3-6}$cycloalkyl or $C_{3-6}$-heterocyclyl;

or a salt thereof.

2. The compound of formula I according to claim 1, wherein:

Cy is a phenyl, cyclohexyl, indanyl, 2,3-dihydrobenzofuranyl or tetrahydroquinolinyl group, each optionally substituted with one, two, or three substituent groups independently selected from —Cl, —F, $C_{1-3}$alkyl, oxo and CN; and $R^1$ and $R^2$ are independently selected from H, $C_{1-3}$alkyl, hydroxy$C_{1-3}$alkyl, —$CH_2NHC(O)OC_{1-4}$alkyl, —$C(O)N(C_{1-4}$-alkyl$)_2$ and —$CH_2OC(O)C_{1-4}$alkyl.

3. The compound of formula I according to claim 1, wherein:

Cy is phenyl optionally substituted with one, two, or three substituent groups independently selected from —Cl, —F, $C_{1-3}$alkyl and CN.

4. The compound of formula I according to claim 1, wherein:

Cy is phenyl substituted with CN and optionally substituted with one or two additional groups independently selected from —Cl, —F and $C_{1-3}$alkyl;

$R^1$ is —$CH_3$; and $R^2$ is —$CH_3$ or —$CH_2OH$.

5. The compound according to claim 4, wherein:
R² is —CH₂OH.
6. The compound according to claim 4, wherein:
R² is —CH₃.
7. The compound according to claim 1 selected from the group consisting of
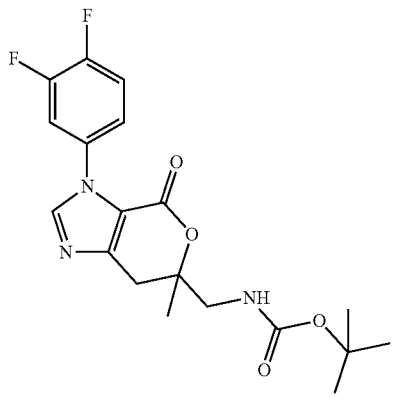
1
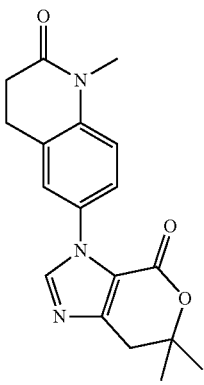
5
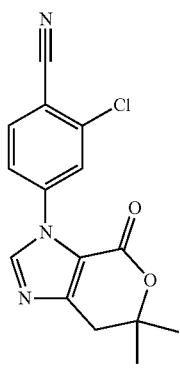
6
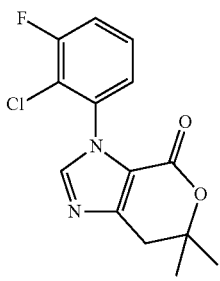
7
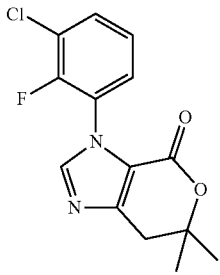
8
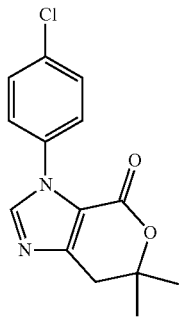
9

-continued
10
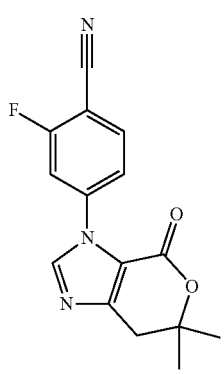
11
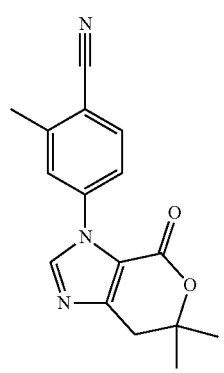
12
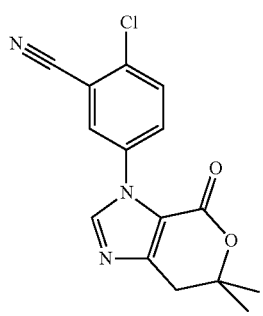
13
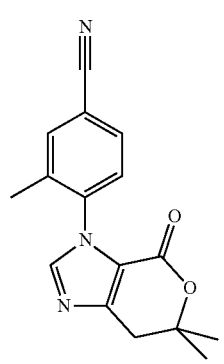
-continued
14
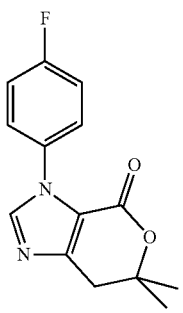
15
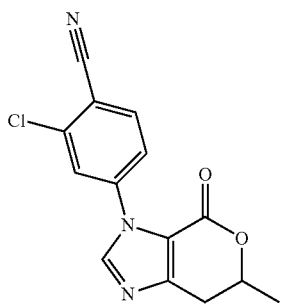
16
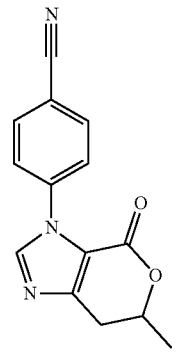
17
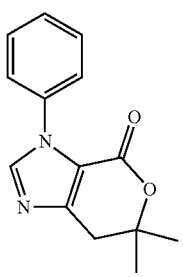
18
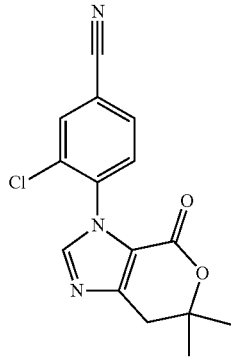

| | |
|---|---|
| 19 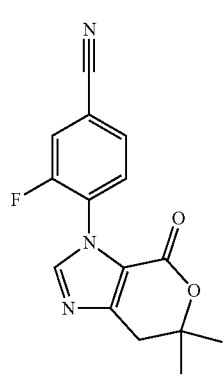 | 24 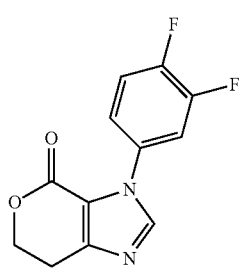 |
| 20 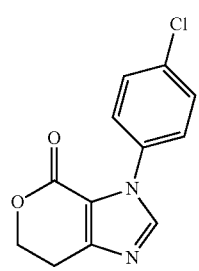 | 25 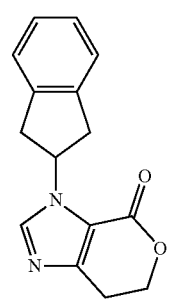 |
| 21 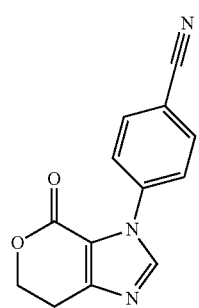 | 26 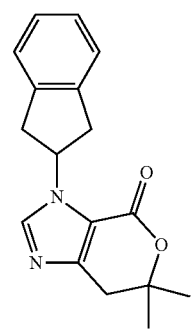 |
| 22 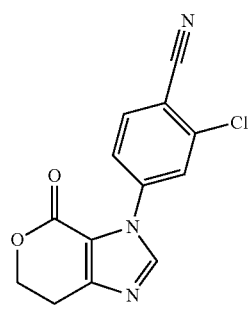 | 27 |
| 23 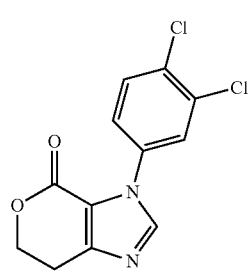 | 28 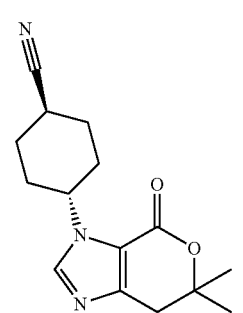 |

-continued
29A
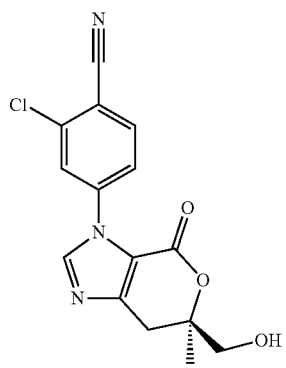
29B
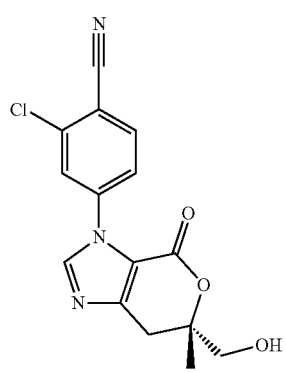
30
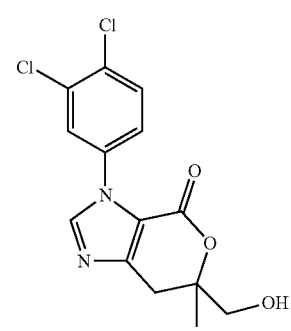
31
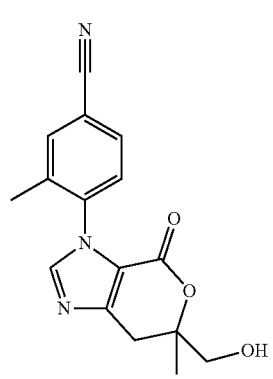
-continued
32
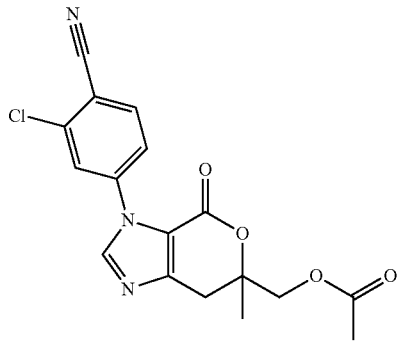
33
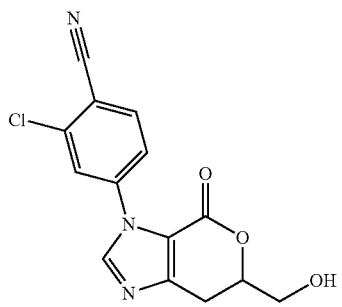
34
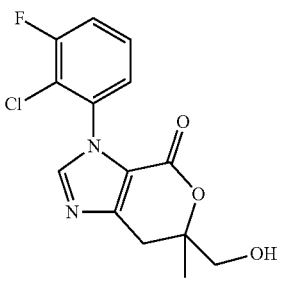
35
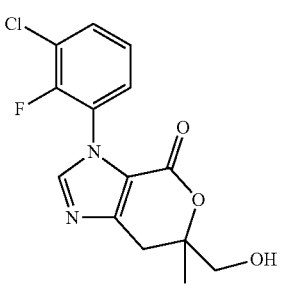
36
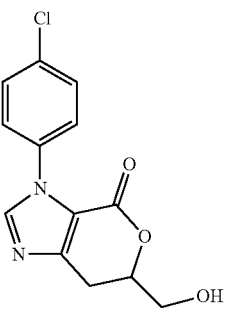

-continued
37 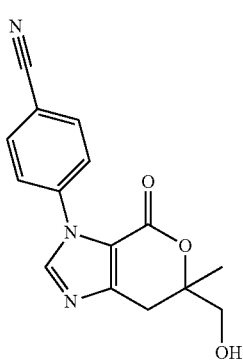
38 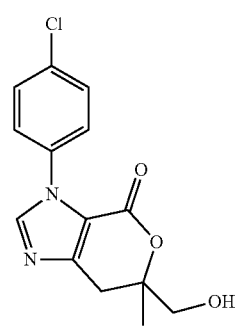
39 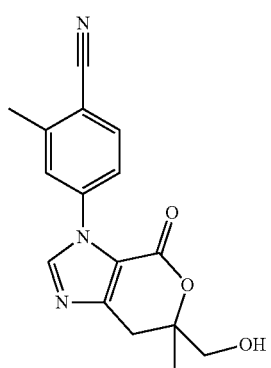
40 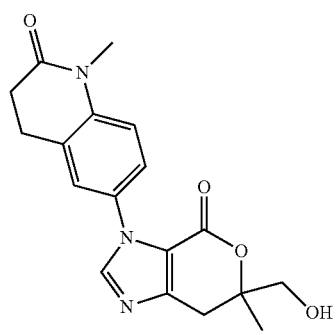
-continued
41 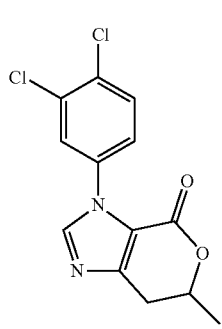
42 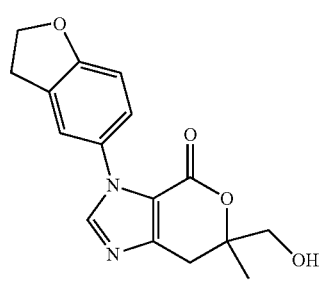
43 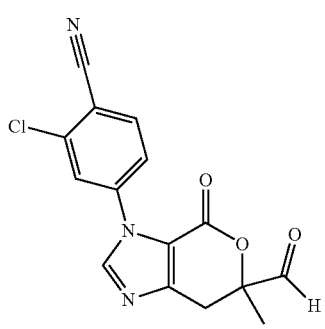
44 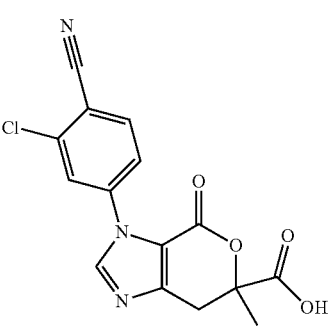
45 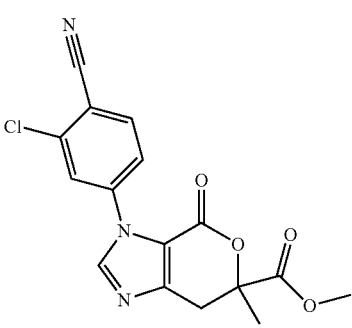

-continued

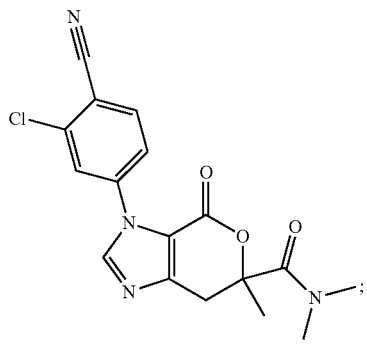

and the pharmaceutically acceptable salts thereof.

8. The compound according to claim 7 selected from the group consisting of compound numbers 1-11, 13, 15, 18, 19, 22, 23, 26, 28, 29A, 29B, 30-33, 35, 39, 41, 42, 45 and 46.

9. A pharmaceutical composition comprising a compound according to claim 1 and a pharmaceutically acceptable excipient or carrier.

10. A method of treating a disease or disorder that can be alleviated by inhibition of aldosterone synthase selected from diabetic nephropathy, glomerulosclerosis, glomerulonephritis, IGA nephropathy, nephritic syndrome, focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism comprising administering a therapeutically effective amount of a compound according to claim 1 to patient in need thereof.

11. The method according to claim 10, wherein the disease or disorder is selected from diabetic nephropathy, glomerulosclerosis, glomerulonephritis, IGA nephropathy, nephritic syndrome and focal segmental glomerulosclerosis (FSGS).

12. The method according to claim 10, wherein the disease is diabetic nephropathy.

13. The compound according to claim 1, wherein the compound is

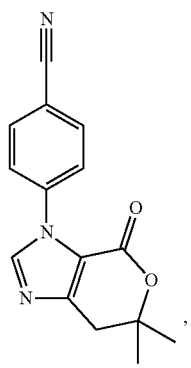 [SMILES: CC1(C)Cc2ncn(-c3ccc(C#N)cc3)c2C(=O)O1]

or a pharmaceutically acceptable salt thereof.

14. The compound according to claim 1, wherein the compound is

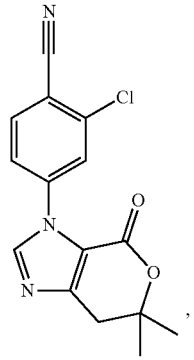 [SMILES: CC1(C)Cc2ncn(-c3ccc(C#N)c(Cl)c3)c2C(=O)O1]

or a pharmaceutically acceptable salt thereof.

15. The compound according to claim 1, wherein the compound is

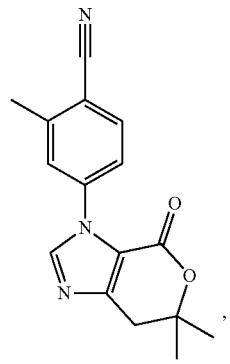

or a pharmaceutically acceptable salt thereof.

16. The compound according to claim 1, wherein the compound is

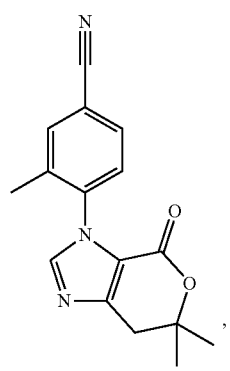

or a pharmaceutically acceptable salt thereof.

17. The compound according to claim 1, wherein the compound is

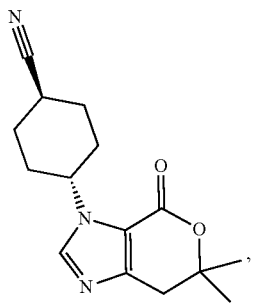 [SMILES: CC1(C)Cc2ncn([C@H]3CC[C@H](C#N)CC3)c2C(=O)O1]

or a pharmaceutically acceptable salt thereof.

18. The compound according to claim 1, wherein the compound is

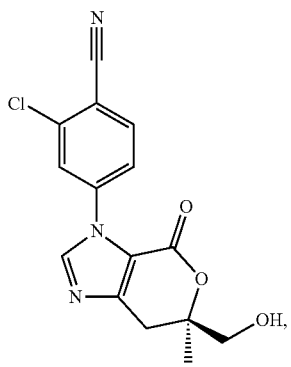 [SMILES: C[C@]1(CO)Cc2ncn(-c3ccc(C#N)c(Cl)c3)c2C(=O)O1]

or a pharmaceutically acceptable salt thereof.

19. The compound according to claim 1, wherein the compound is

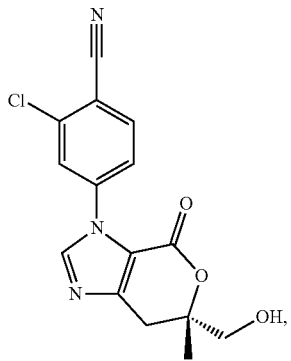 [SMILES: C[C@@]1(CO)Cc2ncn(-c3ccc(C#N)c(Cl)c3)c2C(=O)O1]

or a pharmaceutically acceptable salt thereof.

20. The compound according to claim 1, wherein the compound is

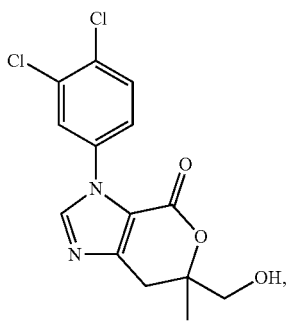 [SMILES: CC1(CO)Cc2ncn(-c3ccc(Cl)c(Cl)c3)c2C(=O)O1]

or a pharmaceutically acceptable salt thereof.

21. The compound according to claim 1, wherein the compound is

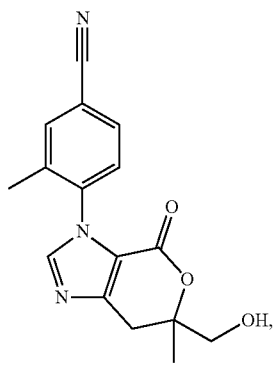 [SMILES: Cc1cc(C#N)ccc1-n1cnc2c1C(=O)OC(C)(CO)C2]

or a pharmaceutically acceptable salt thereof.

22. The compound according to claim 1, wherein the compound is

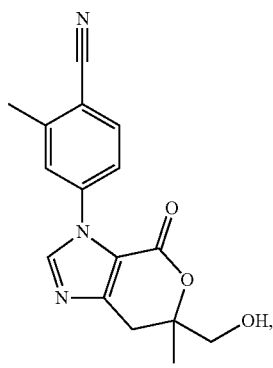 [SMILES: Cc1cc(-n2cnc3c2C(=O)OC(C)(CO)C3)ccc1C#N]

or a pharmaceutically acceptable salt thereof.

23. A pharmaceutical composition comprising the compound according to claim 13, or a pharmaceutically acceptable salt thereof, and at least one pharmaceutically acceptable carrier.

24. A pharmaceutical composition comprising the compound according to claim 14, or a pharmaceutically acceptable salt thereof, and at least one pharmaceutically acceptable carrier.

25. A pharmaceutical composition comprising the compound according to claim 15, or a pharmaceutically acceptable salt thereof, and at least one pharmaceutically acceptable carrier.

26. A pharmaceutical composition comprising the compound according to claim 16, or a pharmaceutically acceptable salt thereof, and at least one pharmaceutically acceptable carrier.

27. A pharmaceutical composition comprising the compound according to claim 17, or a pharmaceutically acceptable salt thereof, and at least one pharmaceutically acceptable carrier.

28. A pharmaceutical composition comprising the compound according to claim 18, or a pharmaceutically acceptable salt thereof, and at least one pharmaceutically acceptable carrier.

29. A pharmaceutical composition comprising the compound according to claim 19, or a pharmaceutically acceptable salt thereof, and at least one pharmaceutically acceptable carrier.

30. A pharmaceutical composition comprising the compound according to claim 20, or a pharmaceutically acceptable salt thereof, and at least one pharmaceutically acceptable carrier.

31. A pharmaceutical composition comprising the compound according to claim 21, or a pharmaceutically acceptable salt thereof, and at least one pharmaceutically acceptable carrier.

32. A pharmaceutical composition comprising the compound according to claim 22, or a pharmaceutically acceptable salt thereof, and at least one pharmaceutically acceptable carrier.

33. The method according to claim 10, wherein the compound of formula (I) is

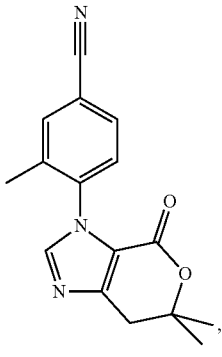

or pharmaceutically acceptable salt thereof.

34. The method according to claim 10, wherein the compound of formula (I) is

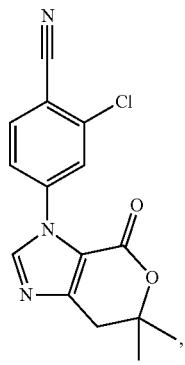 [SMILES: CC1(C)Cc2ncn(-c3ccc(C#N)c(Cl)c3)c2C(=O)O1]

or pharmaceutically acceptable salt thereof.

35. The method according to claim 10, wherein the compound of formula (I) is

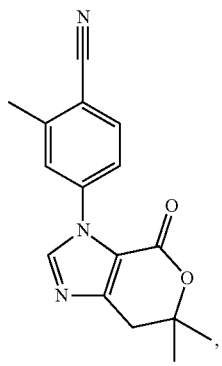

or pharmaceutically acceptable salt thereof.

36. The method according to claim 10, wherein the compound of formula (I) is or pharmaceutically acceptable salt thereof.

37. The method according to claim 10, wherein the compound of formula (I) is

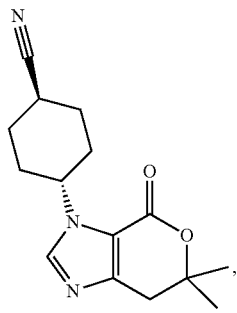 [SMILES: CC1(C)Cc2ncn([C@H]3CC[C@H](C#N)CC3)c2C(=O)O1]

or pharmaceutically acceptable salt thereof.

38. The method according to claim 10, wherein the compound of formula (I) is

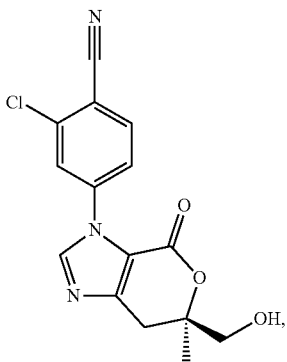 [SMILES: C[C@]1(CO)Cc2ncn(-c3ccc(C#N)c(Cl)c3)c2C(=O)O1]

or pharmaceutically acceptable salt thereof.

39. The method according to claim 10, wherein the compound of formula (I) is

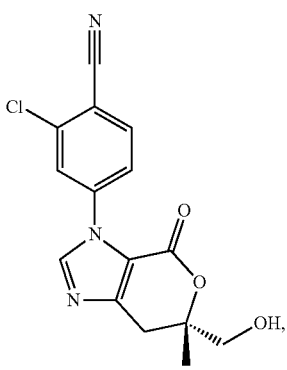 [SMILES: C[C@@]1(CO)Cc2ncn(-c3ccc(C#N)c(Cl)c3)c2C(=O)O1]

or pharmaceutically acceptable salt thereof.

40. The method according to claim 10, wherein the compound of formula (I) is

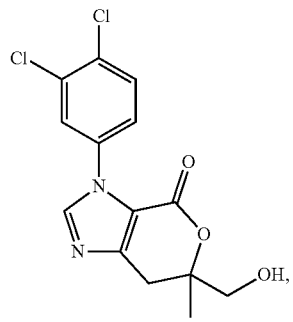 [SMILES: CC1(CO)Cc2ncn(-c3ccc(Cl)c(Cl)c3)c2C(=O)O1]

or pharmaceutically acceptable salt thereof.

41. The method according to claim 10, wherein the compound of formula (I) is

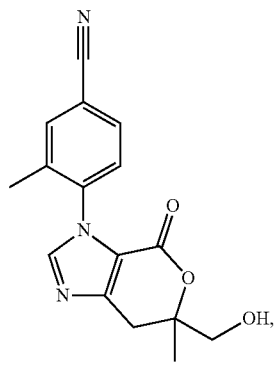 [SMILES: Cc1cc(C#N)ccc1-n1cnc2c1C(=O)OC(C)(CO)C2]

or pharmaceutically acceptable salt thereof.

42. The method according to claim 10, wherein the compound of formula (I) is

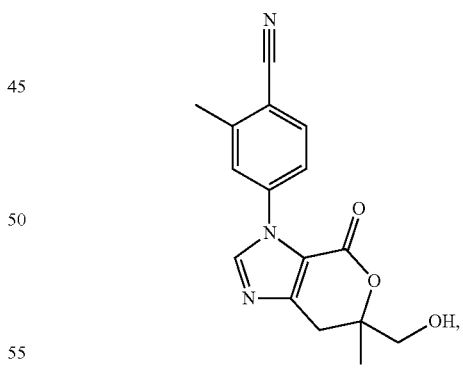

or pharmaceutically acceptable salt thereof.

* * * * *